(12) United States Patent
Di Carlo et al.

(10) Patent No.: US 9,638,620 B2
(45) Date of Patent: *May 2, 2017

(54) SYSTEM FOR DEFORMING AND ANALYZING PARTICLES

(71) Applicant: THE REGENTS OF THE UNIVERSITY OF CALIFORNIA, Oakland, CA (US)

(72) Inventors: Dino Di Carlo, Los Angeles, CA (US); Daniel R. Gossett, Los Angeles, CA (US); Henry T. K. Tse, San Francisco, CA (US); Aram Chung, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/802,293

(22) Filed: Jul. 17, 2015

(65) Prior Publication Data

US 2015/0355073 A1 Dec. 10, 2015

Related U.S. Application Data

(63) Continuation of application No. 14/058,028, filed on Oct. 18, 2013, now Pat. No. 9,151,705.

(Continued)

(51) Int. Cl.
*G01N 33/00* (2006.01)
*G01N 15/14* (2006.01)
(Continued)

(52) U.S. Cl.
CPC ....... *G01N 15/1404* (2013.01); *G01N 15/147* (2013.01); *G01N 15/1434* (2013.01);
(Continued)

(58) Field of Classification Search
CPC .. G01N 15/1404; G01N 33/50; G01N 21/645; G01N 15/147
See application file for complete search history.

(56) References Cited

U.S. PATENT DOCUMENTS

| 5,798,827 A | 8/1998 | Frank et al. |
| 8,935,098 B2 | 1/2015 | Di Carlo et al. |

(Continued)

FOREIGN PATENT DOCUMENTS

| KR | 10-0889617 B1 | 3/2009 |
| KR | 10-0889618 B1 | 3/2009 |

(Continued)

OTHER PUBLICATIONS

Bhagat, Ali Asgar et al., Intertial microfluidics for sheath-less high-throughput cytometry, Biomed. Microdevices 12(2), 187-195 (2010).

(Continued)

*Primary Examiner* — Sam P Siefke
(74) *Attorney, Agent, or Firm* — Vista IP Law Group LLP

(57) ABSTRACT

A system for deforming and analyzing a plurality of particles carried in a sample volume includes a substrate defining an inlet, configured to receive the sample volume, and an outlet; and a fluidic pathway fluidly coupled to the inlet and the outlet. The fluidic pathway includes a delivery region configured to receive the plurality of particles from the inlet and focus the plurality of particles from a random distribution to a focused state, a deformation region defining an intersection located downstream of the delivery region and coupled to the outlet, and wherein the deformation region is configured to receive the plurality of particles from the delivery region and to transmit each particle in the plurality of particles into the intersection from a single direction, a first branch fluidly coupled to the deformation region and configured to transmit a first flow into the intersection, and (Continued)

a second branch fluidly coupled to the deformation region and configured to transmit a second flow, substantially opposing the first flow, into the intersection, wherein the first flow and the second flow are configured to induce extension of one or more particles in the plurality of particles.

16 Claims, 21 Drawing Sheets

Related U.S. Application Data

(60) Provisional application No. 61/718,077, filed on Oct. 24, 2012, provisional application No. 61/718,092, filed on Oct. 24, 2012, provisional application No. 61/719,171, filed on Oct. 26, 2012.

(51) Int. Cl.
  G01N 33/50 (2006.01)
  G01N 21/64 (2006.01)
  G01N 15/00 (2006.01)
  G01N 15/10 (2006.01)

(52) U.S. Cl.
  CPC ..... *G01N 15/1436* (2013.01); *G01N 15/1459* (2013.01); *G01N 15/1484* (2013.01); *G01N 21/645* (2013.01); *G01N 21/6428* (2013.01); *G01N 33/50* (2013.01); *G01N 33/5091* (2013.01); *G01N 2015/0065* (2013.01); *G01N 2015/1006* (2013.01); *G01N 2015/1415* (2013.01); *G01N 2015/1495* (2013.01); *G01N 2021/6439* (2013.01)

(56) References Cited

U.S. PATENT DOCUMENTS

| 9,151,705 B2* | 10/2015 | Di Carlo .............. G01N 33/50 |
| 2006/0139638 A1 | 6/2006 | Muller et al. |
| 2013/0177935 A1 | 7/2013 | Di Carlo et al. |
| 2014/0113324 A1 | 4/2014 | Di Carlo et al. |
| 2016/0231224 A1 | 8/2016 | Di Carlo et al. |

FOREIGN PATENT DOCUMENTS

| KR | 10-0965222 B1 | 6/2010 |
| WO | WO 2004/113908 A1 | 12/2004 |
| WO | WO 2009/069418 A1 | 6/2009 |
| WO | WO 2012/040067 A2 | 3/2012 |

OTHER PUBLICATIONS

Choi, Sungyoung et al., Sheathless hydrophoretic particle focusing in a microchannel with exponentially increasing obstacle arrays, Anal Chem., 80(8):3035-9 (2008).
Cross, Sarah E. et al., Nanomechanical analysis of cells from cancer patients. Nat Nano 2:780-783 (2007).
Di Carlo, Dino et al., Dynamic Single-Cell Analysis for Quantitative Biology, Analytical Chemistry 78:7918-7925 (2006).
Di Carlo, Dino, Inertial microfluidics. Lab Chip 9:3038-3046 (2009).
Di Carlo, Dino et al., Continuous inertial focusing, ordering, and separation of particles in microchannels. Proc Natl Acad Sci USA 104:18892-18897 (2007).
Di Carlo, Dino et al., Particle Segregation and Dynamics in Confined Flows, Phys. Rev. Lett. 102 (2009).
Gossett, Daniel R. et al., Particle focusing mechanisms in curving confined flows, Anal Chem 81:8459-8465 (2009).
Guck, Jochen et al., Optical Deformability as an Inherent Cell Marker for Testing Malignant Transformation and Metastatic Competence. Biophysical Journal 88:3689-3698 (2005).
Lee, Wonhee et al., Dynamic self-assembly and control of microfluidic particle crystals, Proc. Natl. Acad. Sci. U.S.A 107, 22413-22418 (2010).
Mao, Xiaole et al., single-layer planar on-chip flow cytometer using microfluidic drifting based three-dimensional (3D) hydrodynamic focusing, Lab Chip, 9, 1583-1589 (2009).
Oakey, John et al., Particle Focusing in Staged Inertial Microfluidic Devices for Flow Cytometry, Anal. Chem., 82, 3862-3867 (2010).
Park, Jae-Sung et al., Continuous focusing of microparticles using intertial lift force and vorticity via multi-orifice microfluidic channels, Lab on a Chip, 9, 939-48 (2009).
Perkins, Thomas T. et al., Single Polymer Dynamics in an Elongational Flow, Science 276:2016-2021 (1997).
Sraj, Ihab et al., Cell deformation cytometry using diode-bar optical stretchers, J Biomed Opt 15 (2010).
Suresh, S. et al., Connections between single-cell biomechanics and human disease states: gastrointestinal cancer and malaria. Acta Biomater 1:15-30 (2005).
Thery, Manuel et al., Get round and stiff for mitosis. HFSP J 2:65-71 (2008).
Yamada, Masumi et al., Hydrodynamic filtration for on-chip particle concentration and classification utilizing microfluidics Lab Chip, 5, 1233-1239 (2005).
Gossett, D.R. et al., Deformability Cytometry: High-Throughput, Continuous Measurement of Cell Mechanical Properties in Extensional Flow, 14th International Conference on Miniaturized System for Chemistry and Life Sciences Oct. 3-7, 2010, Groningen, The Netherlands (3pages).
PCT International Search Report for PCT/US2011/052041, Applicant: The Regents of the University of California, Form PCT/ISA/210 and 220, dated Apr. 10, 2012 (7pages).
PCT Written Opinion of the International Search Authority for PCT/US2011/052041, Applicant: The Regents of the University of California, Form PCT/ISA/237, dated Apr. 10, 2012 (5pages).
PCT International Preliminary Report on Patentability (Chapter I of the Patent Cooperation Treaty) for PCT/US2011/052041, Applicant: The Regents of the University of California, Form PCT/IB/326 and 373, dated Apr. 4, 2013 (7pages).
Office Action dated Oct. 4, 2013 in U.S. Appl. No. 13/823,109, filed Mar. 14, 2013, inventor: Dino Di Carlo, (22pages).
Dobbe, J.G.G. et al., Measurement of the Distribution of Red Blood Cell Deformability Using an Automated Rheoscope, Cytometry (Clinical Cytometry), vol. 50, pp. 313-325, 2002.
Dylla-Spears, Rebecca et al., Single-molecule detection via microfluidic planar extensional flow at a stagnation point, Lab on a Chip, vol. 10, pp. 1543-1549, Mar. 2010.
Lincoln, Bryan et al., Deformability-Based Flow Cytometry, Cytometry Part A, vol. 59A, pp. 203-209, 2004.
Shelby, Patrick J. et al., A microfluidic model for single-cell capillary obstruction by Plasmodium falciparum-infected erythrocytes, PNAS, vol. 100, pp. 14618-14622, 2003.
Squires, Todd M., Microfluidics: Fluid physics at the nanoliter scale, Rev. of Modern Physics, vol. 77, pp. 977-1026, 2005.
Yap, Belinda et al., Cystoskeletal remodeling and cellular activation during deformation of neutrophils into narrow channels, J. Appl. Physiol, vol. 99, pp. 2323-2330, 2005.
Zheng, Bo et al., Formation of Droplets of Alternating Composition in Microfluidic Channels and Applications to Indexing of Concentrations in Droplet-Based Assays, Anal. Chem., vol. 76, pp. 4977-4982, 2004.
Office Action dated May 6, 2014 in U.S. Appl. No. 13/823,109, filed Mar. 14, 2013, inventor: Dino Di Carlo, (26pages).
Young, Susan M. et al., High-Throughput Microfluidic Mixing and Multiparametric Cell Sorting for Bioactive Compound Screening, J. Biomol Scree, vol. 9, pp. 103-111, 2004.
Notice of Allowance dated Aug. 29, 2014, in U.S. Appl. No. 13/823,109, filed Mar. 14, 2013, inventor: Dino Di Carlo (8pages).
PCT International Search Report for PCT/US2013/065747, Applicant: The Regents of the University of California, Form PCT/ISA/210 and 220, dated Aug. 14, 2014 (6pages).
PCT Written Opinion of the International Search Authority for PCT/US2013/065747, Applicant: The Regents of the University of California, Form PCT/ISA/237, dated Aug. 14, 2014 (9pages).

(56) References Cited

OTHER PUBLICATIONS

Chen, J. et al., Classification of cell types using a microfluidic device for mechanical and electrical measurement on single cells, Lab Chip, 2011, 11, 3174-3181.
Gossett, D.R. et al., Deformability Cytometry: High-Throughput, Continuous Measurement of Cell Mechanical Properties in Extension Flow, 14th International Conference on Miniaturized Systems for Chemistry and Life Sciences Oct. 3-7, 2010, Groningen, The Netherlands, 1382-1384.
Guck, J. et al., Optical Deformability as an Inherent Cell Marker for Testing Malignant Transformation and Metastatic Competence, Biophysical Journal, vol. 88, May 2005, 3689-3698.
Guo, Q., Microfluidic Device for Measuring the Deformability of Single Cells, Doctorate Thesis, The University of British Columbia, Apr. 2012, 1-24 (total 78 pages.
Office Action dated Oct. 28, 2014 in U.S. Appl. No. 14/057,942, filed Oct. 18, 2013, inventor: Dino Di Carlo et al., (21pages).
PCT International Preliminary Report on Patentability (Chapter I of the Patent Cooperation Treaty) for PCT/US2013/065747, Applicant: The Regents of the University of California, Form PCT/IB/326 and 373, dated May 7, 2015 (11pages).
Final Office Action dated Apr. 7, 2015 in U.S. Appl. No. 14/057,942, filed Oct. 18, 2013 (14pages).
Notice of Allowance dated May 20, 2016 in U.S. Appl. No. 14/057,942, filed Oct. 18, 2013, inventor: Dino DiCarlo, (10pages).
Office Action dated Sep. 9, 2015 in U.S. Appl. No. 14/057,942, filed Oct. 18, 2013, inventor: Dino DiCarlo, (16pages).
Examiner's Interview Summay dated Nov. 24, 2015 in U.S. Appl. No. 14/057,942, filed Oct. 18, 2013, inventor Dino DiCarlo, (3pages).
Final Office Action dated Jan. 29, 2016 in U.S. Appl. No. 14/057,942, filed Oct. 18, 2013, inventor: Dino DiCarlo, (14pages).
Advisory Action dated Mar. 30, 2016 in U.S. Appl. No. 14/057,942, filed Oct. 18, 2013, inventor: Dino DiCarlo, (3pages).
Office Action dated May 17, 2016 in U.S. Appl. No. 14/552,256, filed Nov. 24, 2014, inventor: Dino DiCarlo, (36pages).
Chambers, Ann F. et al., Metastasis: dissemination and growth of cancer cells in metastatic site, Nature Reviews cancer, vol. 2(8), p. 563-572, 2002.
The extended European Search Report dated May 30, 2016 in European Application No. 13871771.5-1553, Applicant: The Regents of the University of California (13pages).
European Communication dated Jun. 16, 2016 pursuant to Rules 70(2) and 70a(2) EPC in European Application No. 13871771.5-1553, Applicant: The Regents of the University of California (1page).
Gossett, Daniel R. et al., Leukocyte Mechanophenotyping by Deformability Cytometry, 16th International Conference on Miniaturized Systems for Chemistry and Life Sciences Oct. 28-Nov. 1, 2012, Okinawa, Japan (3pages).
Dudani, Jaideep S. et al., Pinched-flow hydrodynamic stretching of single-cells+, Lab Chip, 2013, 13, 3728.
Bow, Hanson et al., A microfabricated deformability-based flow cytometer with application to malaria, Lab Chip. Mar. 21, 2011; 11(6): 1065-1073. doi:10.1039/c0lc00472c.
Cha, Sukgyun et al., Cell Stretching Measurement Utilizing Viscoelastic Particle Focusing, Anal. Chem., 2012, 84, 10471-10477.
Gossett, Daniel R. et al., Hydrodynamic stretching of single cells for large population mechanical phenotyping, 7630-7635, PNAS, May 15, 2012, vol. 1091, No. 20.

* cited by examiner

TOP VIEW

SIDE VIEW

TOP VIEW

CROSS SECTIONAL VIEW

SYSTEM FOR DEFORMING AND ANALYZING PARTICLES

CROSS-REFERENCE TO RELATED APPLICATIONS

This Application is a continuation of U.S. patent application Ser. No. 14/058,028 filed on Oct. 18, 2013, now issued as U.S. Pat. No. 9,151,705, which claims priority to U.S. Provisional Patent Application No. 61/718,077 filed on Oct. 24, 2012, U.S. Provisional Patent Application No. 61/718,092 filed on Oct. 24, 2012, and U.S. Provisional Patent Application No. 61/719,171 filed on Oct. 26, 2012. Priority is claimed pursuant to 35 U.S.C. §119 and 120. The above-noted Patent Applications are incorporated by reference as if set forth fully herein.

STATEMENT REGARDING FEDERALLY SPONSORED RESEARCH AND DEVELOPMENT

This invention was made with Government support under Grant No. 1150588, awarded by the National Science Foundation and N66001-11-1-4125, awarded by the Space and Naval Warfare Systems Command. The Government has certain rights in the invention.

TECHNICAL FIELD

This invention relates generally to the cytometer field, and more specifically to an improved system and method for deforming and analyzing particles such as cells in the cytometer field.

BACKGROUND

There is growing evidence that cell deformability is a useful indicator of abnormal cytoskeletal changes, and may provide a label-free biomarker for determining cell states or properties, such as metastatic potential, cell cycle stage, degree of differentiation, and leukocyte activation. Clinically, a measure of metastatic potential could guide treatment decisions, or a measure of degree of differentiation could prevent transplantation of undifferentiated tumorigenic stem cells in regenerative therapies. For drug discovery and personalized medicine, a measure of cytoskeletal integrity could allow screening for cytoskeletal-acting drugs or evaluation of cytoskeletal drug resistance in biopsied samples. Cell deformability can further provide insight into mechanotransduction pathways for different cell lines, opening new avenues of discovery in cellular biomechanics. Currently, implementation of these techniques and analyses is cost-prohibitive and labor-intensive, which is a substantial limiting factor in clinical and research applications. Current platforms for cell deformation techniques and analyses suffer from a large number of limitations, including one or more of the following: limited throughput, inconsistency, limited characterization of sample heterogeneity, speed, and labor intensity. In particular, platforms optimized for biophysics research operate at rates of approximately 1 cell/minute, which significantly hampers one's ability to process and analyze a large number of heterogeneous particles.

Thus, there is a need in the cytometer field to create a new and improved system and method for deforming and analyzing particles. This invention provides such a new and improved system and method.

SUMMARY

In another embodiment, a system for deforming and analyzing a plurality of particles carried in a sample volume, the system includes: a substrate defining an inlet, configured to receive the sample volume, and an outlet; and a fluidic pathway fluidly coupled to the inlet and the outlet. The fluidic pathway includes: a delivery region configured to receive the plurality of particles from the inlet and focus the plurality of particles from a random distribution to a focused state, a deformation region defining an intersection located downstream of the delivery region and coupled to the outlet, and wherein the deformation region is configured to receive the plurality of particles from the delivery region and to transmit each particle in the plurality of particles into the intersection from a single direction, a first branch fluidly coupled to the deformation region and configured to transmit a first flow into the intersection, and a second branch fluidly coupled to the deformation region and configured to transmit a second flow, substantially opposing the first flow, into the intersection, wherein the first flow and the second flow are configured to induce extension of one or more particles in the plurality of particles.

In another embodiment, a system for deforming and analyzing a plurality of particles carried in a sample volume, the system includes: a substrate defining an inlet, configured to receive the sample volume, and an outlet; and a fluidic pathway fluidly coupled to the inlet and the outlet. The fluidic pathway includes: a delivery region configured to receive the plurality of particles from the inlet and focus the plurality of particles from a random distribution to a focused state, a deformation region coupled to the outlet and defining an intersection configured to receive and deform one or more particles of the plurality of particles, and a trifurcation fluidly coupled to the delivery region and the intersection of the deformation region by a first branch and a second branch, wherein the delivery region is configured to direct substantially all particles of the plurality of particles into the first branch in a first flow toward the intersection, and wherein the second branch is configured to transmit a second flow, substantially devoid of any particles of the plurality of particles, wherein first flow and second flow at the intersection induces extension of one or more particles of the plurality of particles.

DESCRIPTION OF THE ILLUSTRATED EMBODIMENTS

The following descriptions of the illustrated embodiments of the invention are not intended to limit the invention to this preferred embodiment, but rather to enable any person skilled in the art of flow cytometers to make and use this invention.

1. System

Figure 1:
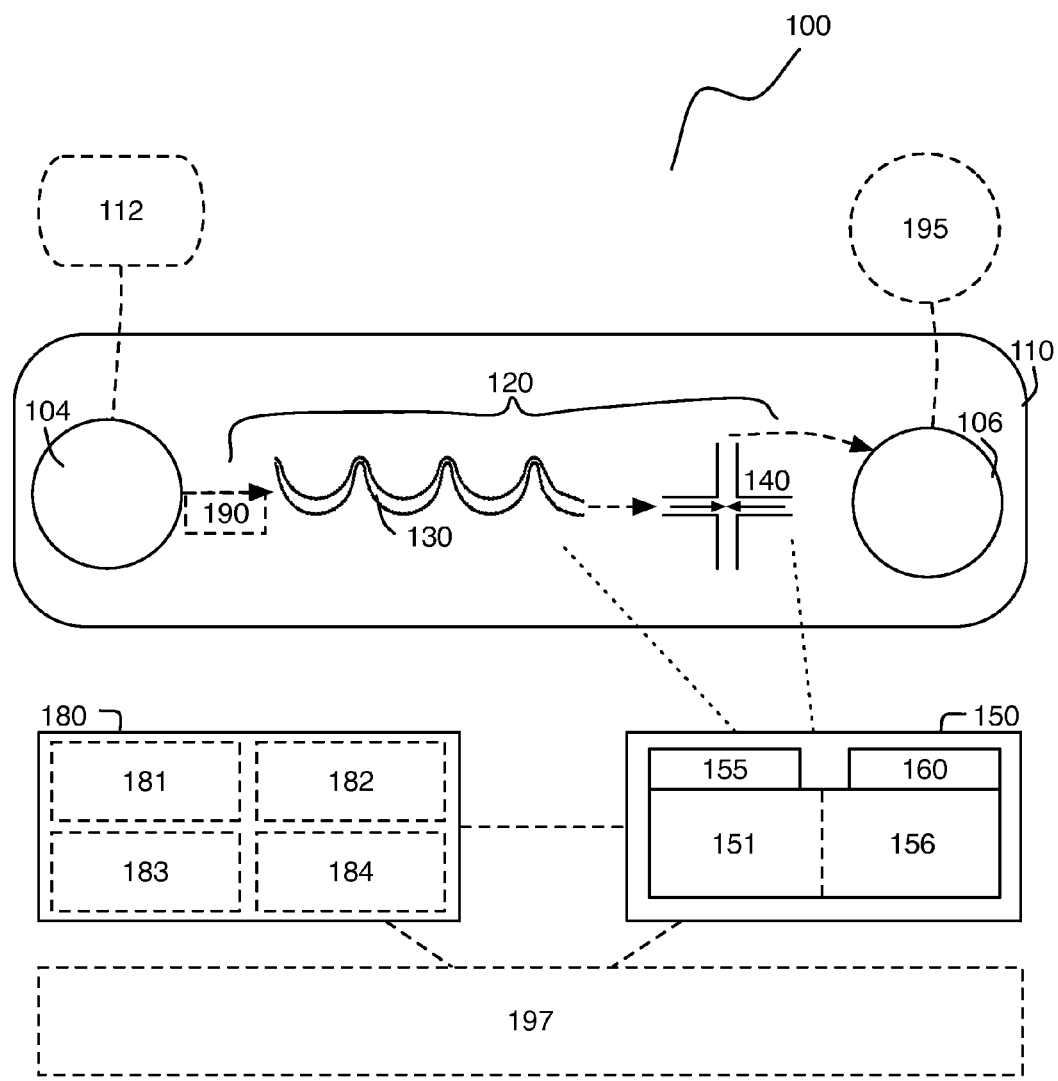
FIG. 1 is a schematic representation of an embodiment of a system for deforming and analyzing particles.

As shown in FIG. 1, a system 100 according to one embodiment is disclosed for deforming and analyzing a plurality of particles carried in a sample fluid. As used herein, the terms "particle" or "particles" are meant to encompass small objects that can be contained within fluid flow. A particle may include a biological object such as a cell or even an organelle. According to this embodiment, the system 100 includes a substrate 110 defining an inlet 104 and an outlet 106; a fluidic pathway 120 fluidly coupled to the inlet 104 and the outlet 106 and defining a delivery region 130 located upstream of a deformation region 140 configured to deform one or more particles that enter the deformation region 140; a detection module 150 including a sensor 155 configured to generate data characterizing the deformation of one or more particles contained within a plurality of particles flowing through the system 100 and a photodetector 160 configured to generate data characterizing fluorescence of each particle in the plurality of particles; and a processor 180 configured to generate an analysis based upon deformation and fluorescence of the one or more particles.

The system 100 functions to enable the deformation of single particles in a high-throughput and consistent manner, with the ability to simultaneously generate and analyze multiple data types characterizing the single particles. Preferably, the system 100 further functions to enable the generation of data that directly correlates surface biomarkers of phenotype with mechanical properties at the single-particle level. This can allow the generation of a direct quantitative comparison between biomolecular properties and mechanical properties. Preferably, the system 100 is used to process and analyze biological particles, such as cells, and in specific applications, the system 100 can be used to analyze leukocyte activation, stem cell differentiation, cellular response to drugs, and cancer cell malignancy by way of correlating cellular deformation with biomolecular phenotypes using fluorescence assays. Besides correlating to biomolecular phenotypes, combining biomolecular and deformability-based data can provide additional classification accuracy. However, the system 100 can alternatively be used to process, deform, and analyze any other suitable biological particle or non-biological particles.

1.1 System—Substrate

Figure 2A:
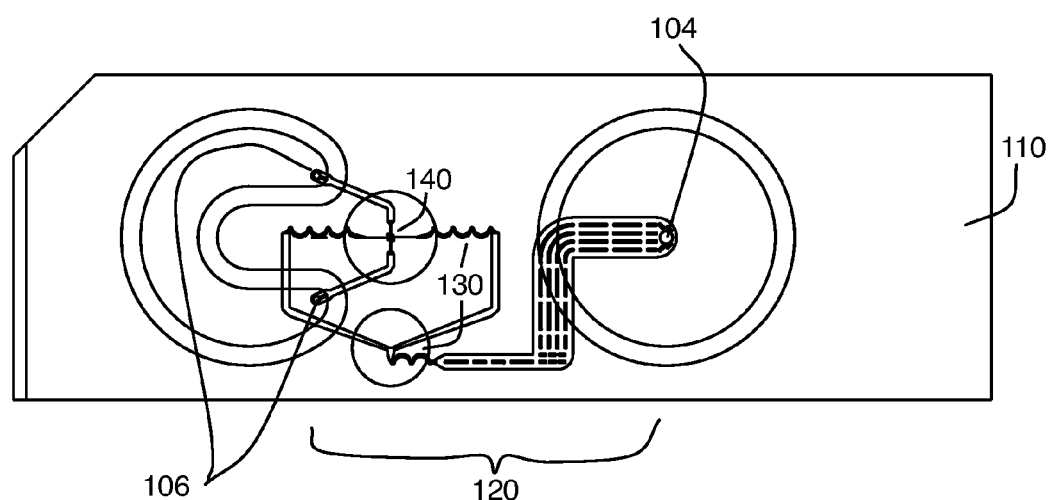
FIGS. 2A and 2B are schematic representations of an embodiment of a portion of a system for deforming and analyzing particles.
Figure 2B:
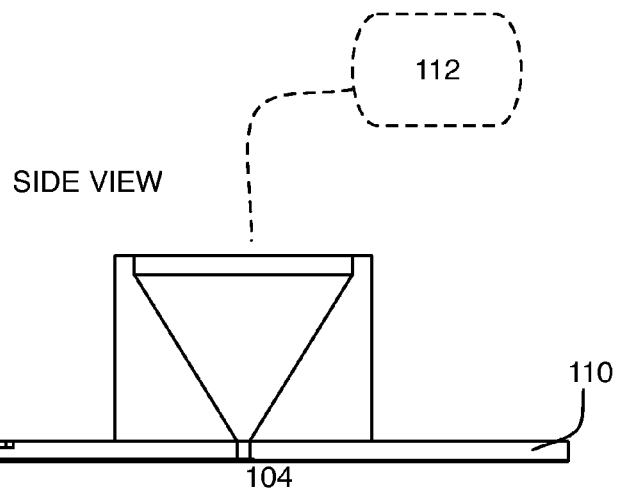

The substrate 110 functions to provide a platform by which particles of interest can be deformed and analyzed. The substrate preferably comprises microfluidic elements that enable deformation of the particles of interest, and facilitates data generation from the deformed particles of interest by defining a suitable configuration of the microfluidic elements relative to other elements of the system 100 (e.g., pump, detection module, waste chamber). In one variation, the microfluidic elements of the substrate include an inlet 104 and an outlet 106 for receiving a sample volume and transmitting a processed sample volume, respectively, from the substrate 110. In a first specific example, as shown in FIGS. 2A and 2B, the substrate 110 includes a single inlet 104 defined at a first surface of one end of the substrate 110 and two outlets 106 defined at an opposite end of the substrate 110. However, other variations of the substrate 110 can comprise any other suitable element(s) in any suitable configuration that facilitates coupling with elements external to the substrate 110 for deforming, processing, and analyzing a sample volume containing particles of interest. For example, the substrate 100 may include multiple inlets 104 and multiple outlets 106. The inlet(s) 104 and outlet(s) 106 of the substrate 110 can be defined at any suitable end, at any suitable surface, and/or within any suitable region of the substrate 110. Furthermore, an inlet 104 can be configured to receive any suitable processing fluid (e.g., sheath fluid, reagent, buffer, wash, etc.) to facilitate sample processing.

In some variations, the substrate 110 can be configured to be a reusable element and in other variations, the substrate 110 can be configured to be a disposable element. In variations wherein the substrate 110 is reusable, the substrate 110 can be configured to couple to a module for washing or flushing the substrate 110 (e.g., through the inlet or outlet) after uses of the substrate. Alternatively, in these variations of a reusable substrate 110, the substrate 110 can be configured to be self-cleaning or self-washing (e.g., using surface coatings, by geometric configuration of fluidic pathways, etc.). In other variations, the substrate can be configured to be reusable for a certain number of uses or until failure (e.g., failure by clogging), and then disposed to be replaced. In any of these variations, the substrate 110 can comprise aligners (e.g., slots, pins, guides, etc.) configured to facilitate alignment of the substrate 110 within the system 100 and relatively to other elements of the system 100. The substrate 110 may be a monolithic substrate or the substrate 110 may be formed from multiple layers that are bonded or otherwise secured to one another to form the appropriate microfluidic elements within the substrate 110.

The inlet 104 functions to receive a sample volume, including a plurality of particles of interest, to initiate processing and analysis of the particles within the substrate 110. Preferably, the inlet 104 is configured to receive the sample volume and the plurality of particles from a fluid delivery module including a pump 112, as shown in FIG. 1; however, the inlet can be configured to receive the sample volume in any other suitable manner. In other variations, the pump 112 can be a syringe pump containing the sample volume and the plurality of particles, or any other fluid pump configured to provide at least one of a positive pressure and a negative pressure, in order to deliver the sample volume and the plurality of particles into the inlet 104. Additionally, the pump 112 can be manually or automatically operated, but is preferably configured to transmit the sample volume into the inlet 104 at a uniform flow rate that can be adjusted. Furthermore, the pump 112 can be coupled to any suitable conduit (e.g., tubing, conduit, manifold) configured to transmit the sample volume (e.g., from a sample well coupled to the substrate) into the inlet 104, and can comprise a valve and/or a pressure sensor in order to control and detect flow parameters. In one specific example, the pump 112 is automatically controlled and configured to provide an adjustable flow rate that enables particle focusing and achieves a desired particle deformation. Alternatively, the pump 112 may be controlled to achieve a particular particle throughput. Furthermore, in still other alternative examples, the pump 112 may be configured to deliver a sample volume including cells (i.e., particles of interest) with a density between 200,000 cells/mL and 8 million cells/mL.

In specific applications with biological particles, the plurality of particles (e.g., cells) can be prepared for fluorescence-based assays prior to delivery into the inlet 104 of the substrate 110. Preferably, the plurality of particles is prepared using an approach that omits fixation, which can affect deformation of the particles in unknown and/or unpredictable ways. The cells are preferably labeled with at least one fluorescently-labeled biochemical probe (e.g., SSEA4 probe, Oct4 probe, TRA-1-60 probe, CD34 probe, CD38 probe, HLA-DR probe, CD64 probe, etc.) bound to cell surface proteins or other biomarkers, which facilitates identification of biomolecular markers that can be extracted as fluorescence data. The cells can additionally be processed with cell-permeable stains to facilitate identification. However, the plurality of particles can be processed in any other suitable manner prior to delivery into an inlet 104, and/or during transmission through any element of the system 100 (e.g., fluidic pathway, etc.).

Preferably, the inlet 104 is configured to form a hermetic seal about the fluid delivery module and/or the pump 112, such that the sample volume does not leak from the inlet 104; furthermore, the inlet 104 is preferably configured to be reversibly coupled to the fluid delivery module and/or the pump 112. However, the inlet 104 can be configured to couple to the fluid delivery module and/or the pump 112 in any other suitable manner. In one variation, the inlet 104 is configured to couple to the pump 112 by a threaded male-female coupling configured to produce a hermetic seal. In another variation, the inlet 104 can additionally or alternatively comprise an o-ring configured to facilitate generation of the hermetic seal. In still other variations, the inlet 104 can additionally or alternatively comprise any other suitable sealant (e.g., resealable septum, silicone sealant, sealing putty) for generation of the hermetic seal.

The outlet 106 functions to transmit the sample volume including the plurality of particles of interest from the substrate 110, after the sample volume has been processed. Preferably, the outlet 106 is configured to transmit the processed sample volume as waste from the substrate 110; however, the outlet 106 can alternatively be configured to transmit the processed sample volume from the substrate 110 for further processing and analysis. In one variation, the outlet 106 can be configured to couple to a waste chamber as seen in FIG. 2A that is configured to receive waste fluids from the outlet 106. In this variation, the waste chamber can be integrated (e.g., of unitary construction, physically coextensive) with the substrate 110, such that the outlet 106 is configured to deliver waste fluids into the waste chamber of the substrate 110. In another variation, the outlet 106 can be configured to couple to a fluid conduit that delivers the processed sample volume to another module for further processing. Similar to the inlet 104, the outlet 106 is preferably configured to form a hermetic seal about a point of coupling (e.g., to a waste chamber, to a module for further processing), and can comprise any one or more of: a male-female threaded coupling, an o-ring, septum, and a sealant that facilitates generation of the hermetic seal. In other variations, however, the outlet 106 can be configured to couple to any other suitable element in any other suitable manner, for example, using one or more microfluidic conduits or channels.

The substrate 110 is preferably composed of an optically transparent material with no autofluorescence, in order to facilitate detection of sample particle characteristics (e.g., deformation characteristics, mechanical properties, fluorescence characteristics) without optical interference from the substrate 110. However, the substrate 110 can be sufficiently transparent and/or composed of a material with sufficiently low autofluorescence in order to enable detection of particle characteristics. Additionally, the substrate 110 can comprise any structures or elements configured to reflect light toward particles passing through the substrate 110, in order to enhance detection of particle characteristics and parameters by a detection module 150. Furthermore, the substrate 110 can include any suitable structure(s) for microfluidic applications, including glass structures, polymeric structures, or composite structures. In one variation, the substrate 110 can be composed of a polymeric material that is processable to form the inlet(s) 104, the outlet(s) 106, and/or any other suitable element(s) of the substrate 110. In a specific example of this variation, the substrate 110 is composed of polydimethylsiloxane (PDMS) contained on a optically transparent solid surface such as glass, with inlet(s) 104, outlet(s) 106, and microfluidic elements defined by a lithographic process (e.g., photolithography), such as a process described in U.S. Pub. No. 2013/0177935, entitled "Method and Device for High Throughput Cell Deformability Measurements", which is incorporated herein in its entirety by this reference. In other variations of this example, substrate features can be additionally or alternatively defined by any other suitable process (e.g., micromachining, molding, etching, 3D printing, etc.). Alternatively, the substrate 110 can comprise or be composed of any other suitable material, processable by any other suitable method to form features of the substrate 110 (e.g., inlets, outlets, fluidic pathways, etc.).

1.2 System—Fluidic Pathway

The fluidic pathway 120, as shown in FIGS. 1 and 2A-2B, is preferably fluidically coupled to the inlet(s) 104 and the outlet(s) 106 of the substrate 110, and functions to facilitate focusing and deformation of the plurality of particles of the sample volume. The fluidic pathway 120 is also preferably configured between the inlet(s) 104 and the outlet(s) 106, such that any pressure differential (e.g., generated by the pump 112) along the fluidic pathway 120 facilitates fluid flow through at least a portion of the fluidic pathway 120. Preferably, the fluidic pathway 120 is at least partially defined within the interior of the substrate 110 (e.g., by a lithographic process, by etching, by micromachining, by 3D printing, etc.); however, the fluidic pathway 120 can be partially or completely defined external to the substrate 110. Preferably, the fluidic pathway 120 comprises a delivery region 130 that is located upstream of a deformation region 140, such that the plurality of particles of the sample volume can be transmitted from an inlet 104, focused within the delivery region 130, and transmitted to the deformation region 140 for deformation and analysis. In this configuration, the delivery region 130 is interposed between the inlet(s) 104 and the deformation region 140.

Figure 3A:
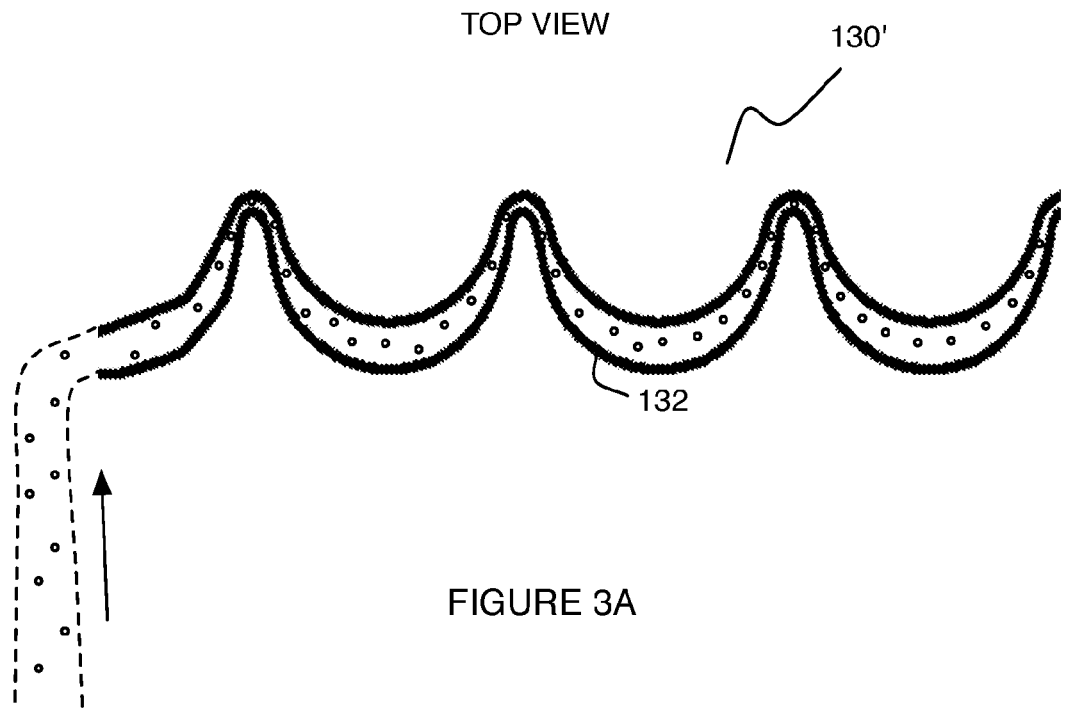
FIGS. 3A and 3B depict a variation of a delivery region in an embodiment of a system for deforming and analyzing particles.
Figure 3B:
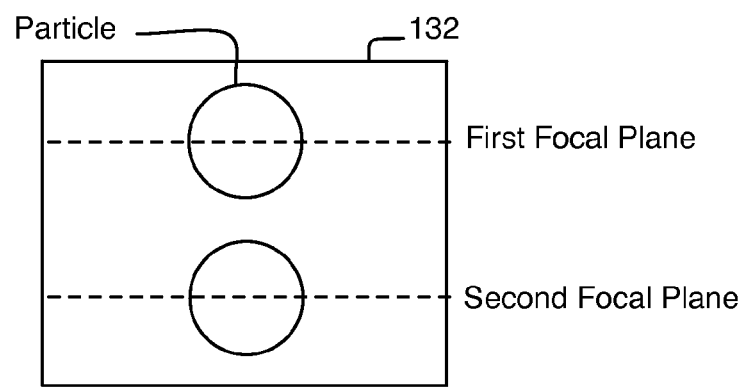

The delivery region 130 functions to focus at least a subset of the plurality of particles into the deformation region 140 along a common equilibrium point or streamline, such that each particle in the plurality of particles experiences sufficiently uniform flow and deformation conditions in a manner that limits experimental variability. Additionally, the delivery region 130 is preferably configured to cooperate with conditions provided by the pump 112, such that the plurality of particles flows in single file at a substantially uniform velocity (e.g., with particle size-dependent fluctuations in velocity in 5-10% range) into the deformation region 140. Alternatively, the delivery region 130 and the pump 112 can be configured to transmit the plurality of particles in non-single file, and/or with any suitable velocity profile (e.g., variable velocity profile) into the deformation region 140. Preferably, the delivery region 130 provides inertial focusing and can comprise at least one curved confined channel 132 configured to provide inertial focusing of the plurality of particles into the deformation region 140. In a first variation of the delivery region 130', an example of which is shown in FIG. 3A, the curved channel 132 can be characterized by a profile described, for example, in D. R. Gossett et al., "Particle focusing mechanisms in curving confined flows," Analytical Chemistry, 81, 8459 (2009), which is incorporated herein in its entirety by this reference. The curved channels 132 may be symmetric or asymmetric although asymmetric curved channels 132 are generally preferred. Furthermore, in this variation, the delivery region 130 can comprise multiple curved confined channels 132 coupled in series, as shown in FIG. 3A, that enable focusing of particles into the deformation region 140. In the first variation of the delivery region 130, the curved channel 132 configuration focuses the plurality of particles along a single projected line, with each particle positioned within one of two focal planes, as shown in FIG. 3B. While this embodiment focuses particles at two focal planes as seen in FIG. 3B, particles at both locations can be imaged using a single detection module 150 that operates at a relatively low magnification. At higher magnifications, image processing may be needed to extract images at the two focal planes for deformation analysis.

Figure 4A:
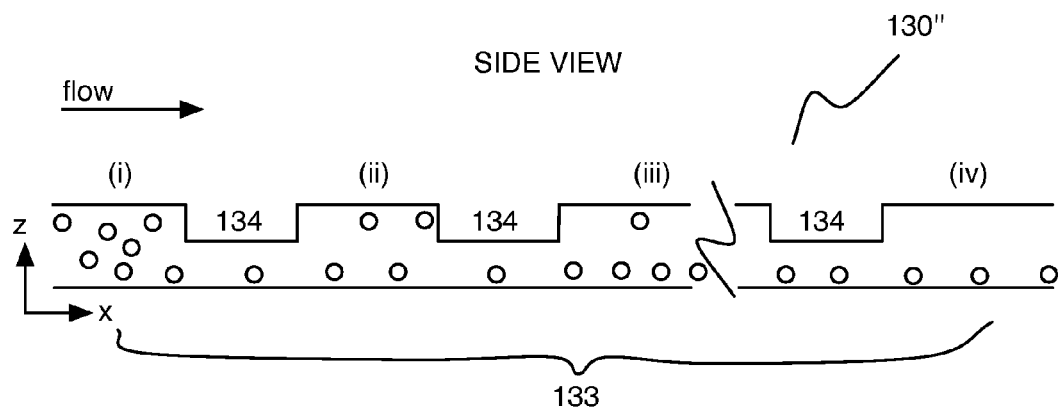
FIGS. 4A and 4B depict a variation of a delivery region in an embodiment of a system for deforming and analyzing particles.
Figure 4B:
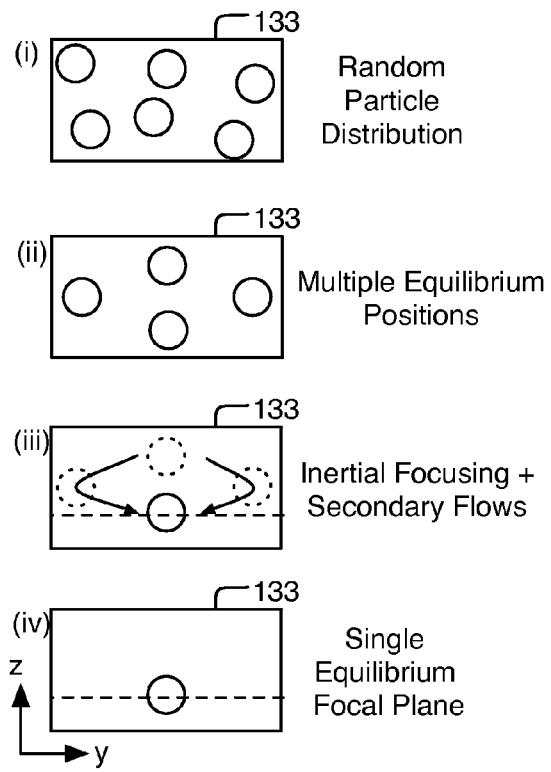

In a second variation of the delivery region 130'', as shown in FIGS. 4A and 4B, the delivery region comprises a straight channel 133 that is interspersed with a plurality of serially arrayed constrictions in height 134, orthogonally arranged relative to the flow direction that provides focusing based upon inertial focusing and geometry-induced secondary flows. The straight channel 133 in the second variation is preferably defined by a low aspect ratio (defined as height divided by width), and the combination of inertial focusing upstream and a pair of local helical secondary flows induced by the height constrictions 134 provides focusing of each particle in the plurality of particles, in sequence, to a single position. In this variation of the delivery region 130'', at a finite Reynolds number (Re), particle migration in the straight channel 133 occurs due to a balance of two inertial lift forces: shear-gradient (FSL) and wall-effect (FWL) lift forces. An interaction between a particle wake and a wall of a channel of the delivery region 130 produces a FWL directed toward the channel centerline, while a parabolic velocity profile causes a shear-gradient induced FSL directed toward a channel wall throughout the channel, except where it is zero at the channel centerline; the balance of the FSL and FWL forces thus leads to well-defined equilibrium particle positions (e.g., along centerlines of channel walls for a channel with a rectangular cross section, as in FIG. 4B. Then, the plurality of height constrictions 134 induce a pair of helical secondary flows configured to induce lateral motions that compete with the inertial lift forces to direct the plurality of particles into a single particle position on a channel wall opposite to the plurality of height constrictions 134, as shown in FIGS. 4A and 4B.

In a specific example of the second variation of the delivery region 130, the straight channel 133 is a rectangular channel with an aspect ratio of approximately 0.5 with a width of 84 micrometers, a height of 41.5 micrometers, and a length of 6 cm. In the specific example, the delivery region comprises thirty (30) constrictions in height that are 21 micrometers in height, 40 micrometers in length, and spaced apart by 1 mm. It should be understood that the particular dimensions discussed above should be regarded as exemplary as other dimensions for the channel and the constrictions may be used. Further, as disclosed herein, a different number of constrictions (e.g., fewer than thirty (30)) may be used to focus the plurality of particles. Prior to entering a height constriction 134, the plurality of particles are focused along centerlines proximal to each of two to four walls of the straight channel 133, depending on aspect ratio. Then, after successively entering each height constriction 134 in the plurality of height constrictions 134, the particles of the plurality of particles deviate toward a single equilibrium position based upon a balance between strong FSL forces and weaker FWL forces. In the specific example, focusing to a single stream defining a single equilibrium position achieved a focusing efficiency (i.e., percentage of particles reaching the equilibrium position) of 99.77% after the plurality of particles entered approximately twenty-five (25) height constrictions of the plurality of height constrictions 134. The height constrictions 134 may project upward from a lower base or, alternatively, project downward from an upper surface. Furthermore, the full width at half maximum (FWHM) defining focusing tightness was 10.995 micrometers in the delivery region for 10 micrometer diameter particles, indicating sufficiently narrow particle focusing. Additionally, focusing in the specific example of the second variation improved with Re, such that at Re=83.33, all particles in the plurality of particles were focused at a single equilibrium position, facilitating measurements by a detection module 150 (e.g., a module defining a single focal depth). In alternatives to the second variation, the straight channel 133 can be replaced by a curved channel 132, such as a curved channel described in the first variation of the delivery region 130 described above. Variations using a curved channel 132 can decrease a total channel length used for the delivery region 130.

In alternative variations, the delivery region 130 can be configured for any one or more of the following types of focusing: hydrodynamic focusing, focusing using a sheath fluid, dielectrophoretic focusing, ultrasonic focusing, magnetic focusing, and any other suitable focusing method. In one example, the delivery region 130 can be configured to direct the plurality of particles into a branch of the fluidic pathway 120 along a common streamline, and simultaneously, to direct portions of the sample volume not including the plurality of particles into other branches of the fluidic pathway 120. As such, the delivery region 130 can be used to separate the plurality of particles from the sample volume, and to utilize a portion of the sample volume for a subsequent use. For example, one subsequent use of a sample volume that does not contain particles includes using the diverted sample volume to squeeze particles. This can be seen, for example, in the trifurcation structure of FIG. 7 whereby two branches 121', 123' divert fluid that is free of particles that is later used in a deformation region 140. Furthermore, the delivery region 130 is preferably configured to direct the plurality of particles along a centerline of a channel of the fluidic pathway 120 to facilitate measurements by a detection module 150; however, the delivery region 130 can be additionally or alternatively be configured to direct the plurality of particles along any suitable portion (e.g., centerline, periphery) of a channel of the fluidic pathway 120 or a branch of the fluidic pathway 120, in order to divert the plurality of particles into specific regions for processing.

Figure 5:
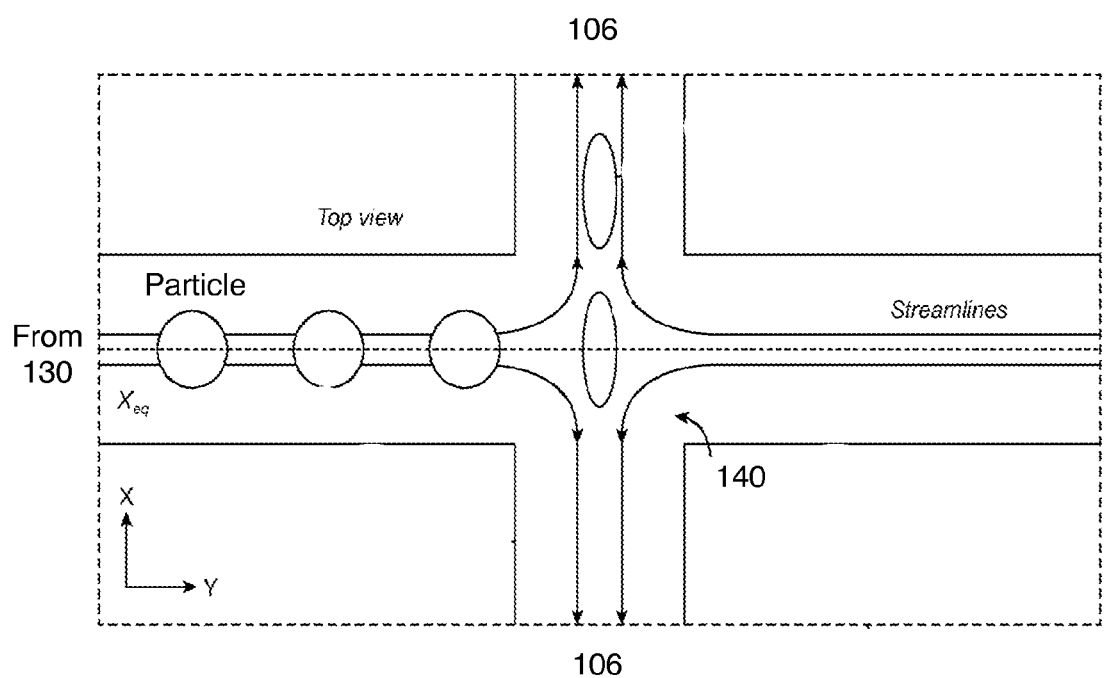
FIG. 5 depicts a variation of a deformation region in an embodiment of a system for deforming and analyzing particles.

The deformation region 140 functions to deform one or more of the plurality of particles by using opposing flows, according to one embodiment, as shown in FIG. 5. In this embodiment, the deformation region 140 is formed at an intersection of opposing flows, whereby a particle entering the intersection of the opposing flows undergoes deceleration and is compressed by the opposing flows, leading to compression of a particle along one axis and extension of each particle along another axis. However, alternative variations of the deformation region can mechanically deform the plurality of particles using any other suitable mechanism. In the embodiment of FIG. 5, the opposing flows are substantially coaxially aligned and flow anti-parallel to each other; however, the opposing flows can be unaligned and/or not flow in anti-parallel directions. In the embodiment of FIG. 5, the particles enter from only one side of the extension region 140. The opposing flow enters the extension region 140 but is free of particles. Preferably, a first flow and a second flow in the opposing flows are generated from the sample volume (i.e., in a self-sheathing manner), such that a first portion of the sample volume is used to generate the first flow and a second portion of the sample volume is used to generated the second flow that opposes the first flow. This can be achieved at branches of the fluidic pathway 120 that are configured to diverge and/or converge (e.g., by way of bifurcations, trifurcations, etc.). This is seen, for example, in the embodiments of FIGS. 1. 2A, 7, 8A, 8B, 9B, 9C, and 9D.

Figure 6A:
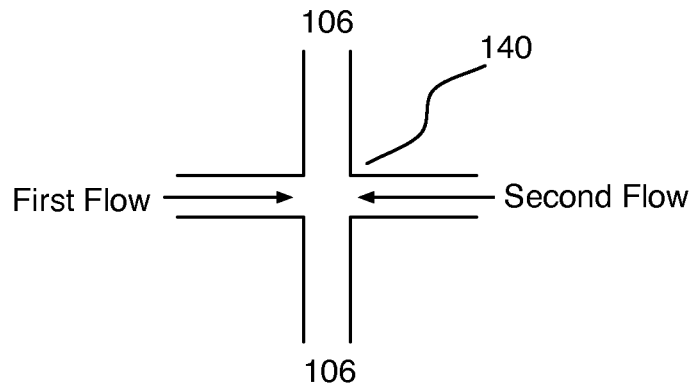
FIG. 6A-6C depict variations of a deformation region in an embodiment of a system for deforming and analyzing particles.
Figure 6B:
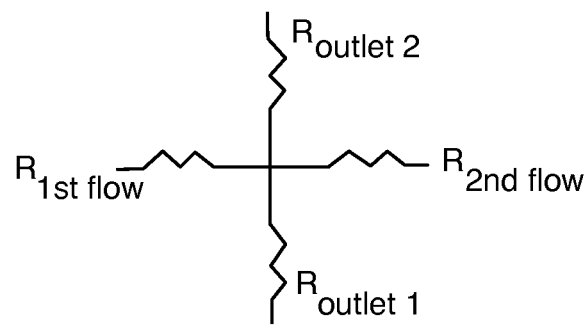
Figure 6C:
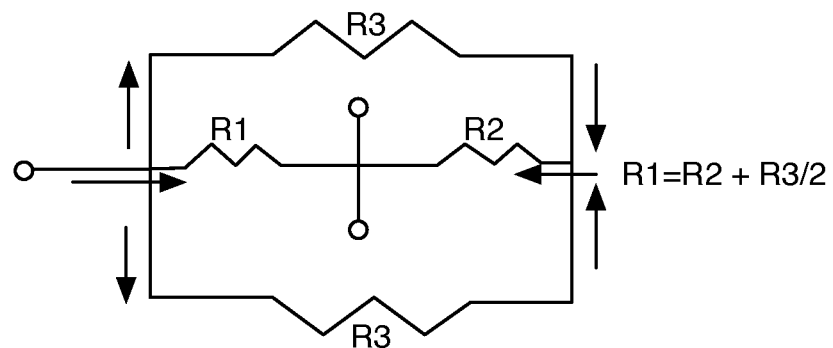

Preferably, the deformation region 140, in cooperation with flow conditions provided by the pump and the delivery region 140, generates a suitable amount of deformation that is substantially uniform across the plurality of particles that have the same mechanical characteristics and does not result in saturation of measurements. For instance, a low flow rate generated by the pump can result in non-uniform deformation at the deformation region 140, and a high flow rate generated by the pump can result in particles being deformed beyond an imaging window and/or particle lysis, leading to measurement saturation. The flow rate(s) used to deform the plurality of particles at the deformation region 140 is preferably associated with a cross-sectional dimension (e.g., diameter, width) of at least a portion of the fluidic pathway 120 (e.g., branch, delivery region, deformation region), with higher flow rates required for larger cross-sections. In one variation, the flow conditions provided by the pump can be governed based upon an analysis of channel resistances (e.g., a ratio of resistances between flow branches), which at least partially depend upon a cross-sectional dimension. In examples of this variation, as shown in FIGS. 6A-6C, a first flow and a second flow in the opposing flows are designed to have a ratio of resistances that generates a suitable opposing flow profile, while maintaining a sufficient number of particles (e.g., 95% of the plurality of particles) within one of the first flow and the second flow. For example, with respect to FIG. 6A, the first flow may include substantially all of the plurality of particles while the second, opposing flow is substantially free of particles. In other examples, a first flow and a second flow in the opposing flows can have matched or unmatched resistances, in order to generate a desired deformation of each particle in the plurality of particles. For example, with reference to FIG. 6B, the resistance of $R_{outlet\ 2}$ may be larger than the resistance of $R_{outlet\ 1}$ in which case a larger percentage of particles will exit the deformation region 140 via $R_{outlet\ 1}$.

In one embodiment, the deformation region 140 receives the plurality of particles from only one flow in the opposing flows that enter the deformation region 140, such that a first flow provides the focused plurality of particles (i.e., from the delivery region 130) and at least one other flow opposes the first flow at an intersection to generate the deformation region 140. The plurality of particles is thus configured to enter the deformation region 140 from a single direction. The single-direction design aspect is important when used in conjunction with fluorescent detection because fluorescent measurements can be made in a single location upstream of the deformation region 140 where the velocity of entering particles is substantially uniform. However, the plurality of particles can alternatively be divided into multiple flows of the opposing flows, and configured to enter an intersection of the opposing flows (i.e., a deformation region 140) from at least two directions for deformation. In variations wherein the plurality of particles is divided into multiple flows, the multiple flows each preferably comprise a delivery region 130 to focus particles along common streamlines prior to deformation. However, any portion of the multiple flows can omit a delivery region 130 in other variations.

Figure 7:
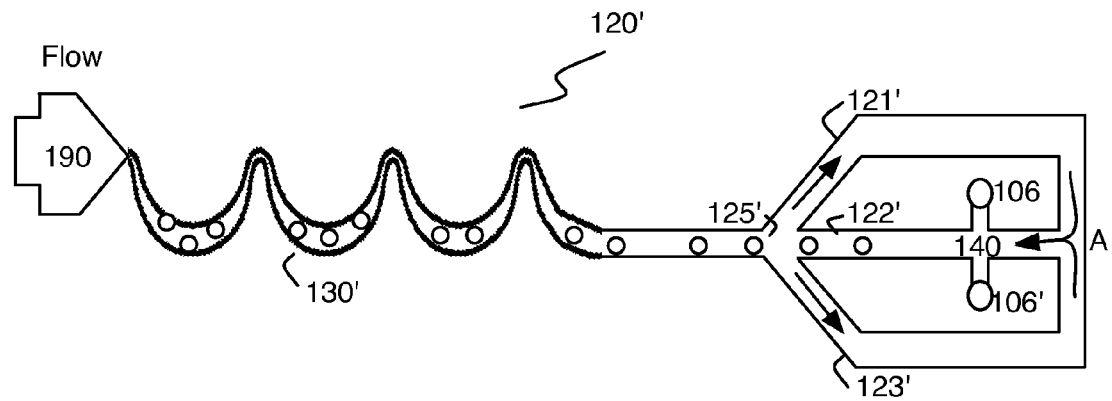
FIG. 7 depicts an example of a fluidic pathway in an embodiment of a system for deforming and analyzing particles.

In one variation, the fluidic pathway 120 comprises a first branch configured to deliver a first portion of the sample volume in a first flow, and a second portion of the sample volume in a second flow, such that sample volume is divided into at least two flows that cooperate to focus and deform the plurality of particles. In a first example of this variation, as shown in FIG. 7, the fluidic pathway 120' includes a trifurcation 125' that divides the sample volume into a first branch 121' in a first flow, a second branch 122' in a second flow, and a third branch 123' in a third flow. In the first example, the delivery region 130' is coupled to the first branch 121', the second branch 122', and the third branch 123' of the trifurcation 125', in a manner that focuses substantially all of the plurality of particles into the second branch 122' of the trifurcation. Additionally, in the first example, the first and the third flows are substantially devoid of particles of the plurality of particles, and the first and the third branches 121', 123' are configured to direct the first and the third flows, respectively, in a direction that opposes the second flow of the second branch 122' (illustrated by arrow A in FIG. 7). In the first example, the intersection of the first, the second, and the third flows at a point of opposition, forms the deformation region 140 for deformation of the plurality of particles. Furthermore, in the first example, the deformation region 140 is configured to couple to a first outlet 106 and a second outlet 106', for transmission of processed sample fluid out of the substrate 110. In variations of the first example, the delivery region 130' can be configured to divert the plurality of particles into any one or more of the first, the second, and the third branches 121', 122, 123', and the fluidic pathway 120' can be configured to couple to any suitable number of inlets 104 and outlets 106 for reception of the sample volume (or other fluids) and transmission of fluids from the substrate 110.

FIG. 6C schematically illustrates the fluidic resistances of the trifurcation embodiment of FIG. 7. R1 represents the fluidic resistance in the second branch 122'. R2 represents the fluidic resistance in the return sheath flow entering the deformation region 140. R3 represents the fluidic resistance in the first and third branches 121', 123'. In this embodiment, as part of the design criteria, $R1=R3/2+R2$.

Figure 8A:
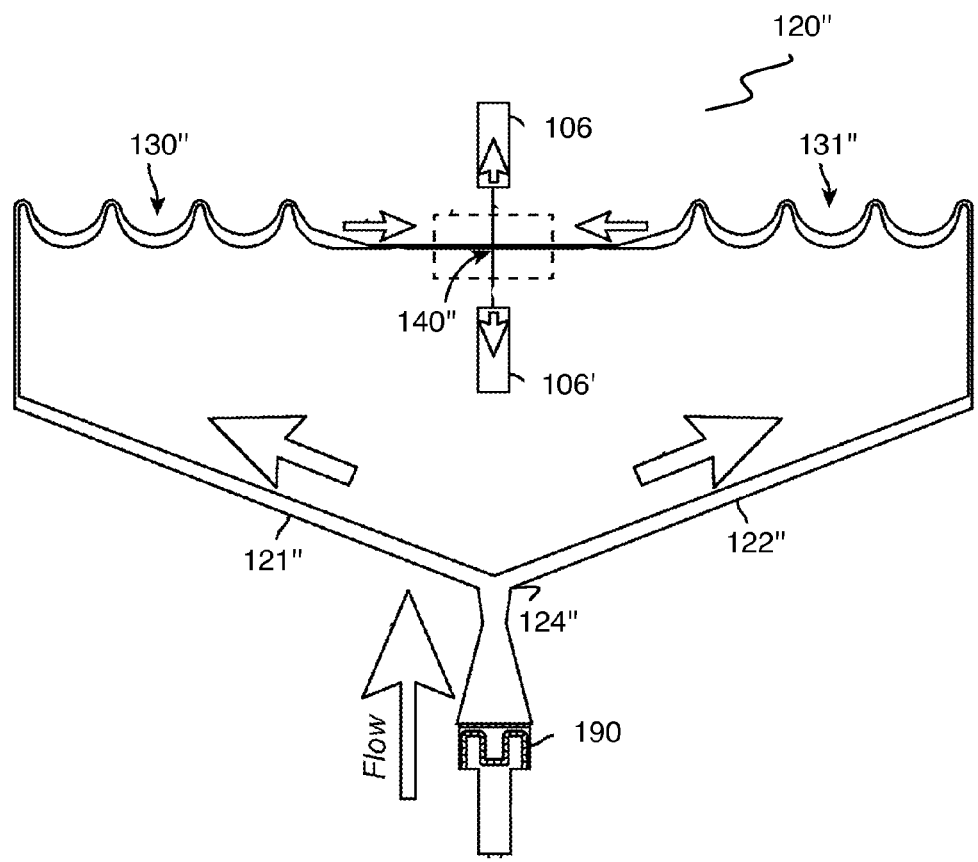
FIG. 8A depicts an example of a fluidic pathway in an embodiment of a system for deforming and analyzing particles.

In another embodiment, as shown in FIG. 8A, the fluidic pathway 120" includes a bifurcation 124" that divides the sample volume into a first branch 121" in a first flow and a second branch 122" in a second flow, wherein the first flow and the second flow each contain a subset of the plurality of particles of the sample volume. In the second example, the delivery region 130" is coupled to the first branch 121" downstream of the bifurcation 124", and a second delivery region 131" is coupled to the second branch 122' downstream of the bifurcation 124", such that the subsets of the plurality of particles are focused within the delivery region 130" and the second delivery region 131". Furthermore, in the second example the first branch 121" and the second branch 122" are configured to direct the first flow and the second flow, respectively, in opposing directions downstream of the delivery regions 130", 131", such that an intersection of the first flow and the second flow defines the deformation region 140". The deformation region 140" in the second example is configured to couple to a first outlet 106 and a second outlet 106', for transmission of processed sample fluid out of the substrate 110. In one alternative embodiment, the fluidic pathway 120" can be configured to divert a first portion of the sample volume (e.g., by inertial focusing, by using multiple inlets), with substantially all particles of the plurality of particles, into the first branch 121", such that the second branch 122" does not receive any particle of the plurality of particles in the second flow (or vice versa). In this variation of the second example, the second delivery region 131" can be omitted, such that the first branch is configured to focus the plurality of particles into the deformation region 140" formed at the intersection of the first and the second branches 121", 122". In this variation of the second example, the plurality of particles is thus configured to enter the deformation region 140 from a single direction.

Figure 8B:
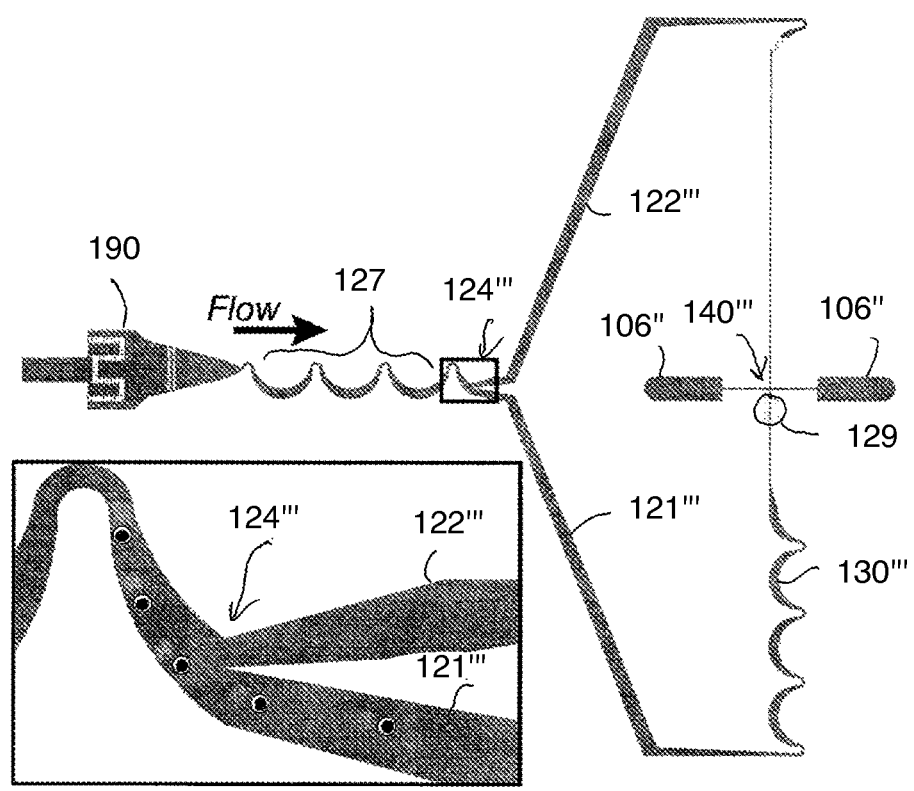
FIG. 8B depicts another example of a fluidic pathway in an embodiment of a system for deforming and analyzing particles.

FIG. 8B illustrates the alternative embodiment discussed above wherein substantially all particles of the plurality of particles are diverted into the first branch 121" ' while the second branch 122' is substantially free of particles. In this example, the bifurcation 124' initiates from a curved portion of an upstream focusing region 127 whereby the particles are preferentially aligned along fluid streamlines that are shunted to the first branch 121'''. The particles then pass through a delivery region 130''' prior to entering an imaging region 129 located immediately upstream of a deformation region 140'. Particles leave the deformation region 140''' via one or both outlets 106", 106'''. A filter 190 is illustrated coupled to the upstream of the focusing region 127.

Furthermore, in alternative variations, each particle in the plurality of particles can be deformed by an opposing flow that has a direction component that is transverse to a prevailing direction of the flow containing the particles. In these alternative variations, at least one opposing flow can be generated with or without using any portion of the sample volume (e.g., by an outside flow that is injected or pumped to generate an opposing flow). In one alternative variation, an opposing flow that is coaxially aligned with, but anti-parallel to a flow containing at least a portion of the plurality of particles, can be generated by an outside flow that is transmitted through an inlet. In another alternative variation, at least one opposing flow can be generated in a direction not coaxially aligned with a flow containing at least a portion of the plurality of particles, such that the opposing flow has a direction component that is transverse to a prevailing direction of the flow containing the particles. In this alternative variation, the opposing flow is preferably substantially orthogonal to a prevailing direction of the flow containing the particles; however, the opposing flow can alternatively be non-orthogonal to and non-parallel to the flow containing the particles.

Figure 9A:
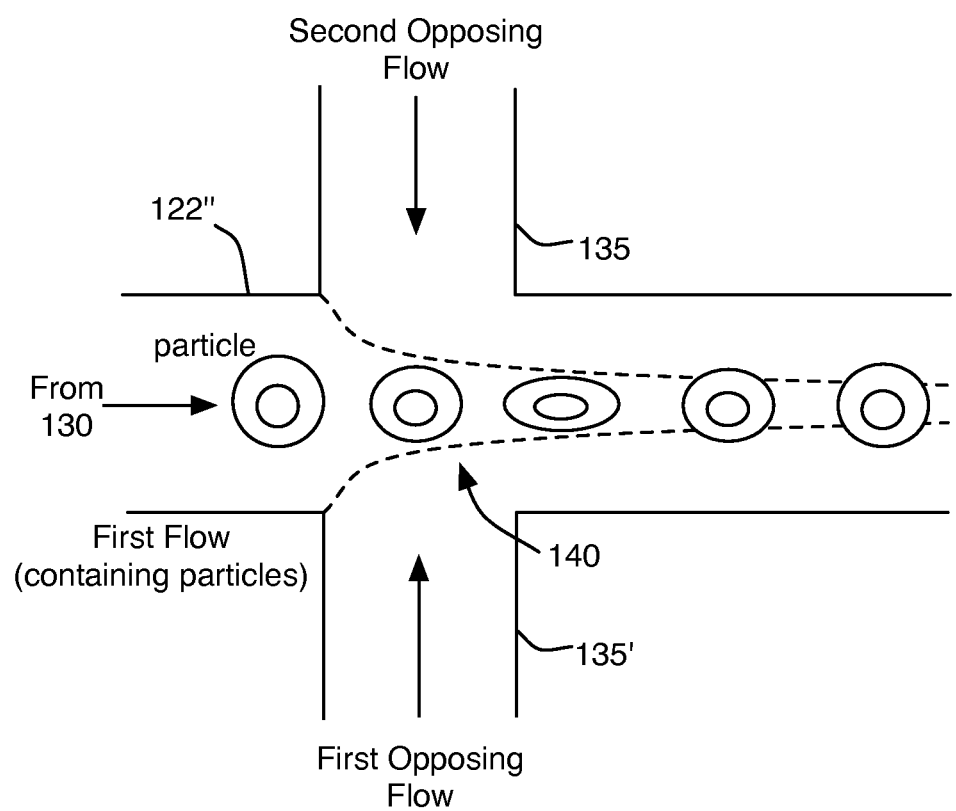
FIG. 9A depicts an alternative example of a deformation region in an embodiment of a system for deforming and analyzing particles.

In one example of an alternative variation, as shown in FIG. 9A, a first flow containing the plurality of particles is configured to enter the deformation region 140 along a first direction via central branch channel 122''', after being focused in an embodiment of the delivery region 130 described above. A first inlet 135 and a second inlet 135' at the deformation region 140 are configured to provide a first opposing flow and a second opposing flow that are anti-parallel (i.e., off-axis) to the first opposing flow. In one embodiment, the first opposing flow and the second opposing flow are both substantially orthogonal to the first flow containing the plurality of particles. The first opposing flow and the second opposing flow in this example are equal and opposite; however, the first opposing flow and the second opposing flow can alternatively be non-equal and/or non-opposite in variations of this example. In addition, while the first inlet 135 and the second inlet 135' are illustrated as being substantially orthogonal to the axis of the first flow containing the plurality of particles in other alternative embodiments, the first inlet 135 and the second inlet 135' may intersect in the deformation region 140 in an off-axis manner yet not be substantially orthogonal to the axis of first flow.

Figure 9B:
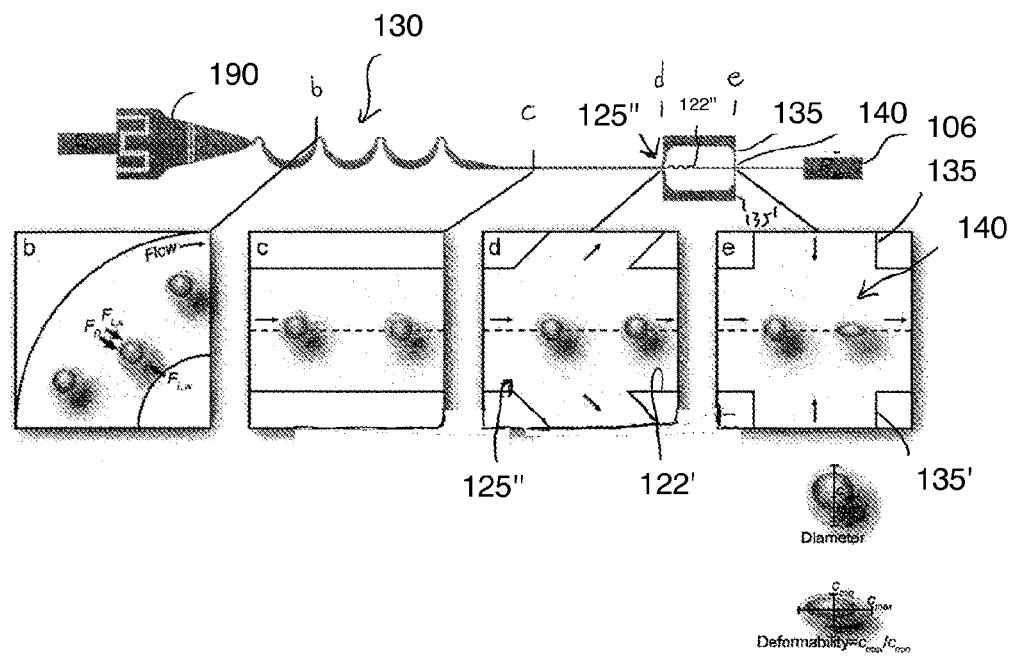
FIG. 9B depicts an example of a fluidic pathway in an embodiment of a system for deforming and analyzing particles using the deformation region illustrated in FIG. 9A.

In one embodiment of FIG. 9A, the fluid that enters the first inlet 135 and the second inlet 135' are siphoned off from an upstream channel that contains the focused particles as seen in FIG. 9B. Because the particles are aligned in the center of the channel due to focusing, side streams can be siphoned off the main flow while letting the focused particles remain in the central branch channel 122''. This particular embodiment is referred to as hydropipette aspiration (HA). The branch channels 135, 135' are subsequently returned to apply a pinching flow at the deformation region 140. Particles are then deformed by the rejoining cell-free (in some embodiments) "sheath" fluid. In contrast with deformability cytometry (DC) whereby cells are subject to a head-on flow and quickly slowed and then accelerated in a transverse direction, the HA device and method is able to achieve a much higher particle throughput. For example, a throughput of 65,000 cells/sec. has been achieved using this design compared to a throughput of around 2,000 cells/sec. achieved using the DC design.

FIG. 9B illustrates an example of a fluidic pathway that utilizes the off-axis configuration illustrated in FIG. 9A. As seen in FIG. 9B, fluid containing the plurality of particles passes first through a filter 190. The outlet of the filter 190 is coupled to a delivery region 130 as described herein that is used to substantially focus the plurality of particles along a common axis as seen inset image at point c in the fluidic pathway. The particles then enter a trifurcation 125". The particles continue along via central branch channel 122" while a portion of the substantially particle-free fluid is shunted to inlets 135, 135' where they recombine with the central branch channel 122' in the deformation region 140 to squeeze and deform the particles as illustrated. The particles continue on in the same direction to outlet 106.

Furthermore, the first opposing flow and the second opposing flow can be generated from the sample volume by siphoning portions of the sample volume (e.g., into a trifurcation or bifurcation that rejoins at the deformation region), or by flows (e.g., injected sheath flows) not generated from the sample volume. In this example, the particles are thus compressed in a direction substantially orthogonal to a direction in which the particle flows, and extends along the direction in which the particle flows. In the configuration provided in this example, particles do not undergo substantial deceleration (e.g., slow down or stop) upon entering the deformation region 140, and the throughput of the system 100 can be increased because multiple particles of the plurality of particles can enter the deformation region 140 simultaneously. Furthermore, a variable range of forces used to deform particles of the plurality of particles can be generated by the first opposing flow and the second opposing flow, by modulating flow parameters of any one or more of the first flow, the first opposing flow, and the second opposing flow. Small forces used to deform the particles can, in particular, be interesting for probing intrinsic particle properties and/or properties of smaller particles (e.g., <10 micrometers in diameter), and can provide insight into membrane elasticity, particle relaxation behavior and other properties of particles that are difficult to assess with large deformation forces.

In still other variations, the delivery region 130 and the deformation region 140 can be configured using any suitable number of branches and in any other suitable manner that enables focusing of the plurality of particles and deformation of the plurality of particles. For example, a variation of the fluidic pathway 120 can comprise multiple delivery regions 130 configured upstream and downstream of a deformation region 140, such that the plurality of particles is focused before and after deformation. In other examples, multiple branches (e.g., more than two branches) can be configured to convene upon the deformation region 140, in order to provide alternative modes of deformation. In still other examples, the plurality of particles can be configured to enter a first deformation region 140 configured to provide deformation from flows that are orthogonal to a direction of the flow carrying the plurality of particles, and can be configured to subsequently enter a second deformation region 140' configured to provide a deformation force from a flow that is anti-parallel to a flow carrying the plurality of particles. Additionally or alternatively, the plurality of particles can be configured to be actively sorted or directed (e.g., by focusing, by flow diversion, based upon channel resistance), into a specific outlet 106. This example could facilitate additional processing of the plurality of particles, as enabled by uniform flow conditions within the additional delivery region 130 and/or active sorting downstream of the deformation region 140.

Figure 9C:
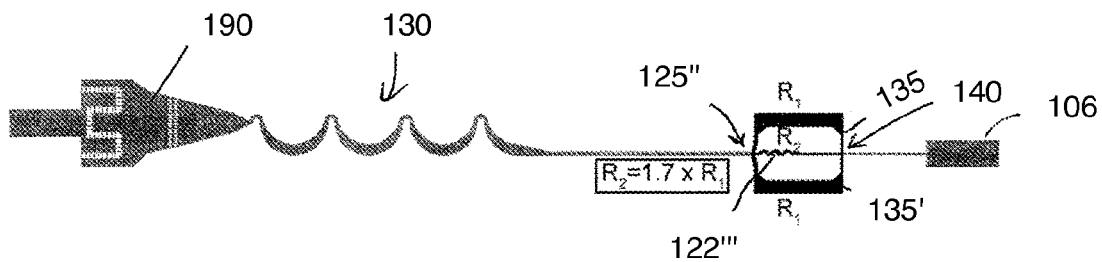
FIG. 9C illustrates the fluidic pathway of FIG. 9B with the resistances labeled for various branch and inlet channels.

FIG. 9C illustrates the fluidic pathway of FIG. 9B with the resistances labeled for the central branch channel 122" and inlets 135, 135' for the deformation region 140 according to one design. As seen in FIG. 9C, R2=1.7*R1. This leads to a decreased fraction of flow down the central branch channel 122" but allows for sufficient Reynolds number for efficient inertial focusing. The outer branches have a lower resistance to allow for a higher flow rate and velocity. This enables a larger squeezing flow on the cells as they pass through the deformation region 140.

Figure 9D:
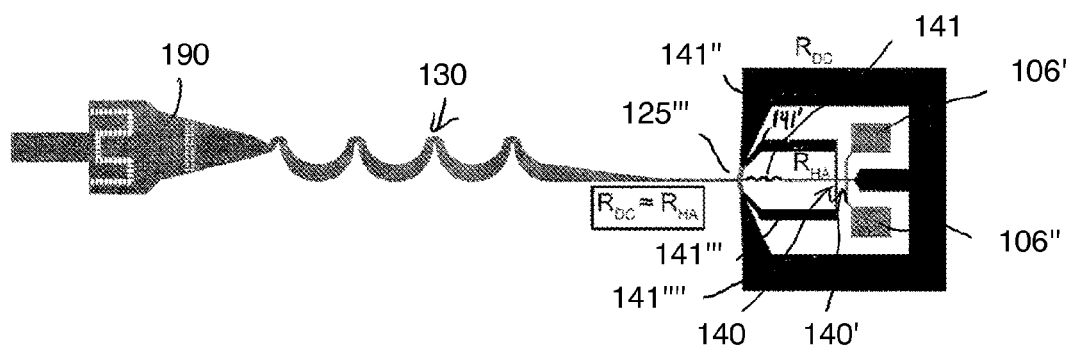
FIG. 9D illustrates an embodiment of a fluidic pathway that combines off-axis squeezing at a first deformation region followed by a secondary deformation region in which particles are subject to deformation at an intersection of opposing flows.

FIG. 9D illustrates an embodiment of a fluidic pathway that combines off-axis squeezing at a first deformation region 140 followed by a secondary deformation region 140' in which particles are subject to deformation at an intersection of opposing flows. In this embodiment, fluid containing the plurality of particles passes first through a filter 190. The outlet of the filter 190 is coupled to a delivery region 130 as described herein that is used to substantially focus the plurality of particles along a common axis. The particles then enter a junction 125''' of five (5) branch channels 141, 141', 141", 141''', 141''''. Central branch channel 141 contains substantially all the particles. Outer branch channels 141', 141", 141', and 141'''' are substantially free of particles and contain portions of fluid shunted from junction 125' Inner branches 141', 141''' recombine with the central branch channel 141 in an off-axis manner to squeeze the particles at the first deformation region 140. The particles continue to a second deformation region 140' whereby fluid from branch channels 141", 141'''' recombine and intersect with the central branch channel 141 in an opposing flow. Particles passing through this second deformation region 140' can then exit the fluidic pathway via one or both outlets 106', 106".

Figure 9E:
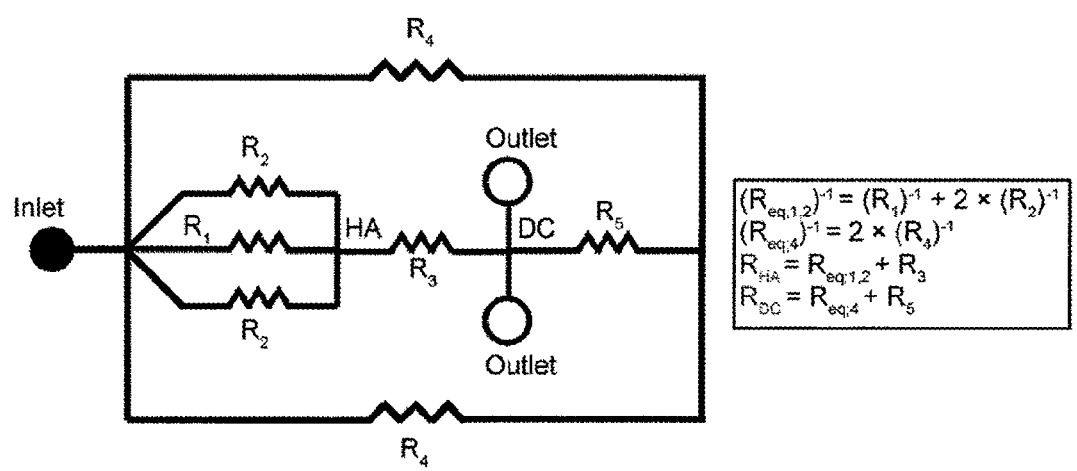
FIG. 9E illustrates a simplified resistor diagram of the combined HA-DC device of FIG. 9D.

FIG. 9E illustrates a simplified resistor diagram of the combined design of FIG. 9D that uses off-axis squeezing of particles (hydropipette aspiration or "HA") in conjunction with deformability cytometry ("DC"). Tuning of resistance is used to ensure equal flow through the two branches of channels creating the extensional flow (RDC and RHA). In this embodiment, RDC≈RHA.

Figure 9F:
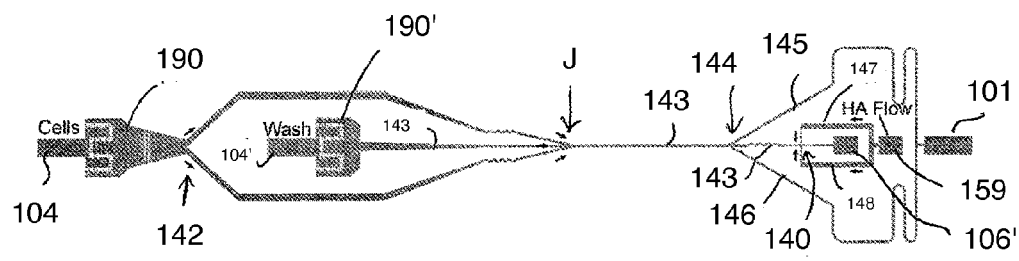
FIG. 9F illustrates another embodiment of a fluidic pathway in which hydropipette aspiration is combined with rapid inertial solution exchange for integrated sample preparation and analysis.

FIG. 9F illustrates another embodiment of a fluidic pathway in which hydropipette aspiration is combined with rapid inertial solution exchange for integrated sample preparation and analysis. In the embodiment of FIG. 9F, a solution containing a plurality of particles is delivered to inlet 104 which then passes through a filter 190. The outlet of the filter 190 terminates in a bifurcation 142 that then recombine in an anti-parallel, off-axis junction J with a central channel 143 fluidically coupled to a wash inlet 104'. As seen in FIG. 9F, a filter 190' is interposed between the outlet of the wash inlet 104' and the central channel 143. The central channel 143 continues until another trifurcation 144 that results in a first branch channel 145, a second branch channel 146 and a continuation of the central channel 143 which may include a focusing or delivery region as described herein. The first and second branch channels 145, 146 are configured to siphon off a portion of fluid flow within the central channel 143. In the embodiment of FIG. 9F, the first and second branch channels 145, 146 act as waste channels which are fluidically coupled to outlet 106. A deformation region 140 is formed downstream of the trifurcation 144 by an intersection of the central channel 143 as well as first and second side channels 147, 148. The first and second side channels 147, 148 are oriented substantially orthogonal to the central channel 143 and are coupled to an inlet 159 that is configured to be fluidically coupled to a pressurized source of fluid. In this regard, sheathing fluid enters inlet 159 and passes into channels 147, 148 which then recombine with the central channel 143 at the deformation region 140. This fluid flow effectuates side squeezing or sheathing of the particles as described herein. After passing through the deformation region 140, the particles can then exit the device via outlet 106'.

Figure 9G:
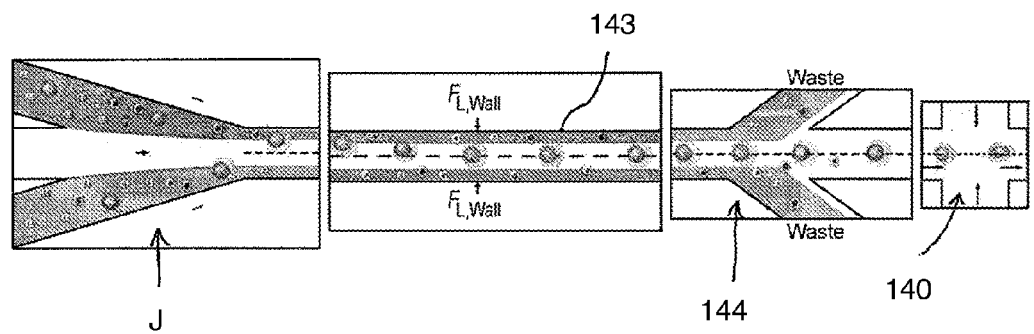
FIG. 9G illustrates series of magnified images of selected regions of the device of FIG. 9F.

FIG. 9G illustrates series of magnified images of selected regions of the device of FIG. 9F. As seen in FIGS. 9F and 9G, in this particular example, a solution containing a mixture of cells (e.g., a blood sample containing a mixture of cells) is delivered to the inlet 104. A wash solution is delivered to the wash inlet 104'. The wash solution may include, for example, phosphate buffered saline (PBS). At the junction J, the outer channels that combine with the central channel 143. After the junction J, in the central channel 143 size-dependent lift forces act upon the larger cells (e.g., cancer cells) to transfer them to the central wash solution contained in the central channel 143. Still referring to FIG. 9F, when the cells reach the trifurcation 144, the smaller blood cells (e.g., white blood cells) are siphoned off to the first and second branch channels 145, 146. The cancer cells continue on in the central channel 143 past the trifurcation 144. Meanwhile, during operation of the device, a solution such as PBS is delivered to the inlet 159 using a pump or the like to create the squeezing sheathing flow at the deformation region 140. At or adjacent to the deformation region 140, the cells can be imaged using a detection module 150 (described in more detail below) that can generate a morphology dataset and/or fluorescent dataset for the cells.

1.3 System—Detection Module

As shown in FIG. 1, the detection module 150 includes an imaging subsystem 151 and a fluorescence subsystem 156, and functions to generate a morphology dataset characterizing deformation of each particle, and a fluorescence dataset characterizing fluorescence of each particle in the plurality of particles. Preferably, the deformation region 140 substantially coincides with a field of view of the at least one of the imaging subsystem 151 and the fluorescence subsystem 156, and additionally, the detection module 150 is preferably configured to capture a field of view extending beyond the deformation region 140. As such, the imaging module 151 and the fluorescence module 155 can be configured to focus upon any suitable region including and extending before or beyond the deformation region 140. For example, in some embodiments, fluorescent images are obtained prior to the particles entering the deformation region 140. Preferably, the detection module 150 generates the morphology dataset and the fluorescence dataset simultaneously; however, the detection module 150 can alternatively be configured to generate the morphology dataset and the fluorescence dataset non-simultaneously (e.g., sequentially). In variations wherein the detection module 150 generates the morphology dataset and the fluorescence dataset simultaneously, the detection module 150 is preferably configured such that light (e.g., white light) used to generate the morphology dataset does not interfere with generation of the fluorescence dataset. Interference can take the form of unwanted excitation of fluorescent labels and/or saturation of fluorescence detectors (e.g., photodetectors) during generation of the fluorescence dataset.

Figure 10A:
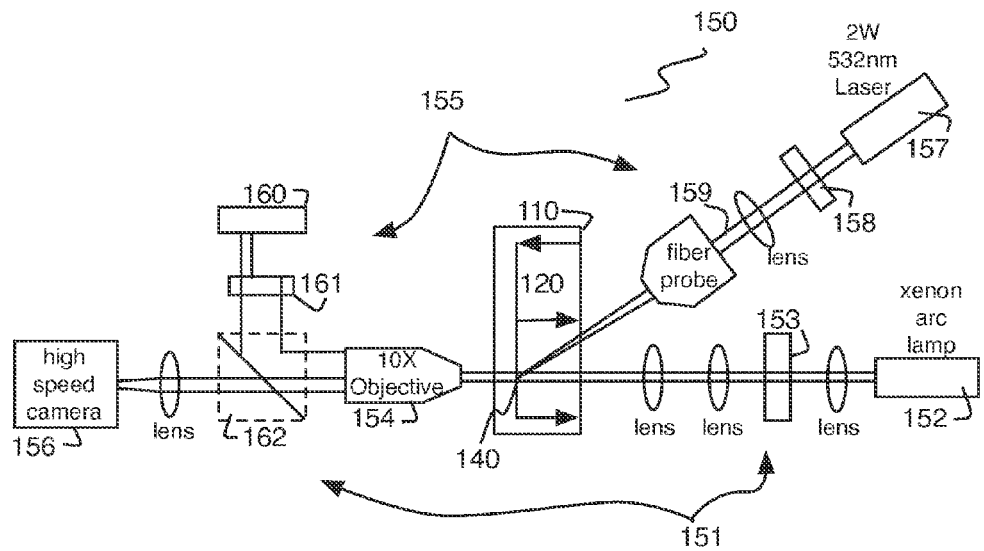
FIGS. 10A-10C depict variations of a detection module in an embodiment of a system for deforming and analyzing particles.

The imaging subsystem 151 functions to generate a morphology dataset characterizing deformation of the particles. Referring now to FIG. 10A, the imaging subsystem 151 preferably comprises a first light source 152 and a first filter 153 configured to transmit light from the first light source 152, through the deformation region 140 and onto an objective lens 154, the objective lens configured to magnify light from the deformation region onto an image sensor 155 for generating the morphology dataset. The imaging subsystem 151 can additionally comprise any suitable number of lenses, for example, for focusing light from the first light source 152 through the first filter 153, for focusing light from the first filter 153 onto the deformation region 140, and for focusing light from the objective lens 154 onto the image sensor 154. The lenses thus function as collection and condensing optics elements, and preferably comprise aspheric lenses; however, the lenses can alternatively comprise plano-convex lenses and/or any other suitable lenses configured to collect and condense light.

The first light source 152 functions to provide enough illumination for generating a morphology dataset at the image sensor 155, without producing unwanted excitation of fluorescent labels at the plurality of particles and/or saturation of a fluorescence detector (e.g., photodetector). As such, the first light source 152 preferably provides a specified range of wavelengths that minimally overlaps with range of wavelengths of fluorescent emission generated in response to fluorescence subsystem 156. The first light source 152 thus preferably provides a sufficient intensity of light that enables proper illumination during short exposure times used in high-speed image data capture. As such, the first light source 152 can be filtered by the first filter 153, in order to reduce interference at a photodetector of the fluorescence subsystem 156 while still providing sufficient illumination at the image sensor 155. In a first variation, the first light source 152 is a xenon light source, which can be used in high-speed imaging applications and fluorescence imaging. Alternatively, the first light source 152 can comprise a halogen light source and/or any other suitable light source in other variations. Furthermore, variations of the detection module 150 can include interchangeable/adjustable light sources, in order to provide varying ranges of light wavelengths, varying intensities of light, and/or any other suitable varying light parameter.

The first filter 153 functions to filter light from the first light source 152 and to transmit filtered light toward the deformation region 140, in order to avoid spectral overlap between the imaging subsystem 151 and the fluorescence subsystem 156. As such, the first filter 153 is preferably coaxially aligned with the first light source 152, in order to properly filter light from the first light source 152. Preferably, the first filter 153 is a bandpass filter configured to only pass light that does not excite fluorophores at the plurality of particles, and additionally, to only pass light that is not detected by a photodetector of the fluorescence subsystem 156. In a specific example, the first filter is configured to filter out wavelengths around 532 nm and around 580 nm, in order to not excite fluorescent labels bound to particles and to avoid light interference at a photodetector of the fluorescence subsystem 156 respectively. In alternative variations the first filter 153 can comprise a lowpass filter, a highpass filter, and/or any other suitable filter for filtering interfering light wavelengths. Furthermore, variations of the detection module 150 can comprise interchangeable filters for filtering light from the first light source 152.

The objective lens 154 functions to receive light from the first filter 153 and passing through the deformation region 140 and to magnify light onto an image sensor 155, in order to facilitate generation of a morphology dataset characterizing deformation of each particle in the plurality of particles. The objective lens 154 is preferably substantially aligned between the first filter 153 and the image sensor; however, the objective lens 154 can alternatively have any other suitable configuration relative to other elements of the detection module 150. The objective lens is preferably characterized by a magnification that enables an entire deformed particle of the plurality of particles to be captured within a window defined by the image sensor 155, wherein the desired magnification depends upon the focal length of the objective lens and/or focal length(s) of any additional optics element(s) (e.g., tube lens), and the position of the image sensor 155 relative to the objective lens and/or optics element(s). In a specific example, the objective lens provides a 10× magnification; however, in other variations, the objective lens can provide any other suitable alternative magnification. In variations, the detection module 150 can include interchangeable/adjustable objective lenses 154, in order to provide an adjustable magnification. Different levels of magnification can enhance the morphology dataset generated at the image sensor 155, by providing, for example, magnification of features not seen at all magnification levels.

The image sensor 155 functions to receive light from the deformation region 140 and passing through the objective lens 154, in order to generate a morphology dataset characterizing deformation of each particle in the plurality of particles. Preferably, the image sensor 155 is substantially aligned with the objective lens 154; however, the image sensor 155 can have any other suitable configuration relative to other elements of the detection module 150. The image sensor 155 can be integrated into a high-speed/high framerate imaging module (e.g., camera), configured to generate image data that captures multiple stages of deformation for each particle in the plurality of particles. As such, specifications of the image sensor 155 and the light source are preferably codependent in order to provide sufficient light parameters (e.g., intensity) for image data generation. The image sensor 155 can comprise a variation of the image sensor described in U.S. Pub. No. 2013/0177935, entitled "Method and Device for High Throughput Cell Deformability Measurements", which is incorporated herein in its entirety by this reference; however, the image sensor 155 can comprise any other suitable image sensor for generating the morphology dataset.

The fluorescence subsystem 156 functions to generate a fluorescence dataset characterizing the fluorescence (or absence of fluorescence) of each particle in the plurality of particles. The fluorescence subsystem 156 can thus comprise a second light source 157 and a second filter 158 configured to transmit light from the second light source 157, through a fiber optic unit 159, through a portion of the fluidic pathway 120, and onto an objective lens 154, the objective lens 154 configured to magnify light from the fluidic pathway 120 onto a photodetector 160 for generating the fluorescence dataset. Light from the fluidic pathway 120 can further be passed through a third filter 161 prior to reception at the photodetector 160, in order to reduce or eliminate effects of interfering wavelengths of light.

The second light source 157 functions to provide excitation wavelengths of light, and to transmit light at excitation wavelengths toward each particle in the plurality of particles in a portion of the fluidic pathway 120. The second light source preferably directs light toward the second filter 158 and the fiber optic unit 159, onto a portion of the fluidic pathway 120, such that fluorescent labels bound to particles passing through the portion of the fluidic pathway 120 are excited by excitation wavelengths of light. In response, the excited fluorescent labels emit emission wavelengths of light, indicative of biomolecular characteristics of the particles, which can be detected at a photodetector 160. The second light source 157 is preferably a light source that provides a specific excitation wavelength of light, and can be a laser (e.g., a 532 nm laser). However, the second light source 157 can alternatively be configured to provide a range of excitation wavelengths of light. In one variation, the second light source 157 can be a broad-spectrum light source (e.g., white light LEDs) that transmits light through at least one excitation filter to generate a specific wavelength or range of wavelengths of light for fluorescent labels(s) excitation. In variations including the excitation filter(s) and a broad-spectrum light source, the excitation filter(s) can be interchangeable in order to provide an adjustable excitation wavelength or an adjustable range of excitation wavelengths.

The second filter 158 functions to modify a parameter of light transmitted from the second light source 157, in order to condition light provided by the second light source 158. The second filter 158 is preferably aligned between the second light source 157 and the fiber optic unit 159; however, in variations omitting the fiber optic unit 159, the second filter 158 can be aligned with the second light source 157 or can have any other suitable configuration. The second filter 158 is preferably a neutral density filter, which is configured to modify or reduce an intensity of light transmitted from the second light source 157. As such, the neutral density filter can function to prevent signal saturation due to high-intensity light, and can additionally function to protect sensitive elements of the detection module 150 from high-intensity light. The second filter 158 can, however, comprise any other suitable filter for conditioning light from the second light source 157.

The fiber optic unit 159 functions to redirect light transmitted through the second filter 158 from the second light source 157, in order to satisfy space requirements of the system 100. Furthermore, the fiber optic unit 159 can function to alter a beam shape (e.g., by a fiber collimator to produce a more spatially uniform beam), and can facilitate translation by coupling to a mount for fine resolution translation in one or more directions (e.g., two dimensions by an x-y mount). As such, the fiber optic unit 159 can include a fiber coupler coupled to a fiber optic-fiber probe assembly that allows light to be transmitted through the fiber-optic-fiber probe assembly. The fiber probe is preferably configured to direct light into a portion of the fluidic pathway through which the plurality of particles pass, such that fluorescent labels bound to the plurality of particles can be properly excited. The portion of the fluidic pathway can comprise the deformation region 140, such that the detection module 150 is configured to simultaneously or nearly simultaneously capture deformation and fluorescence characteristics at the same location along the fluidic pathway; however, the portion of the fluidic pathway can alternatively comprise any other suitable region of the fluidic pathway, for example, a region upstream of the deformation region 140 and downstream of a delivery region 130, or any other suitable region of the fluidic pathway. In one variation, light from the second light source 157 can be directed toward a region immediately upstream of the deformation region (e.g., 100 micrometers to 1 mm upstream), wherein flow conditions are sufficiently uniform. In some variations, wherein space is less of a constraint, the fluorescence module 156 can omit the fiber optic unit 159, light from the second light source 157 through the second filter 158 can be transmitted directly in a straight line from the second light source 157 to the portion of the fluidic pathway 120. Some variations of the fluorescence subsystem 156 can, however, omit the fiber optic unit 159 and instead comprise beam steering mirrors to translate a beam provided by the second light source 157 in multiple dimensions and/or a movable stage (e.g., x-y stage) configured to facilitate translation of a beam in one or more directions.

Similar to the objective lens of the imaging subsystem 151, the objective lens 154 functions to receive light from the second filter 158 passing through the portion of the fluidic pathway 120, and to magnify light onto a photodetector 160, in order to facilitate generation of a fluorescence dataset characterizing fluorescence of each particle in the plurality of particles. The objective lens 154 can be positioned between the fiber probe of the fiber optic unit 159 and the photodetector 161 in any suitable configuration relative to other elements of the detection module 150. The objective lens is preferably characterized by a magnification that enables an entire fluorescing particle of the plurality of particles to be captured within a window defined by the photodetector 160, wherein the desired magnification depends upon the focal length of the objective lens and the position of the photodetector 160 relative to the objective lens 154. In a specific example, the objective lens provides a 10× magnification; however, in other variations, the objective lens can provide any other suitable alternative magnification. In variations, the detection module 150 can include interchangeable/adjustable objective lenses 154, in order to provide an adjustable magnification.

The photodetector 160 functions to receive light emitted upon excitation of fluorescent labels bound to particles of the plurality of particles. The photodetector 160 additionally functions to facilitate generation of a fluorescence dataset characterizing fluorescence characteristics for each particle in the plurality of particles. As such, the photodetector 160 is preferably configured to detect ultraviolet, visible, and infrared light, emitted from excited fluorescent labels. In one variation, the photodetector 160 can comprise a photomultiplier configured to operate by a photoelectric effect upon reception of incident light; however, in other variations, the photodetector 160 can include any other suitable photodetector configured to detect any suitable wavelength of light, by any other suitable mechanism.

As described earlier, the fluorescence module 150 can include a third filter 161 configured to filter light prior to reception at the photodetector 160. The third filter 161 thus functions to reduce or eliminate any effect of interfering light generated from any source (e.g., the first light source 152). Preferably, the third filter 161 is substantially aligned with the photodetector 160, such that incident light on the photodetector 160 is configured to pass through the third filter 161. Additionally or alternatively, the third filter 161 can be configured along any suitable portion of a light path from the objective lens 154 to the photodetector 160. The third filter 161 preferably comprises a bandpass filter; however, the third filter 161 can alternatively or additionally comprise a lowpass filter or a highpass filter.

Preferably, the imaging subsystem 151 and the fluorescence subsystem 155 are integrated, in order to reduce space and cost demands of the detection module 150. As such, in some variations, the imaging subsystem 151 and the fluorescence subsystem 155 can share elements. In one such variation, the imaging subsystem 151 and the fluorescence subsystem 155 can share a single light source, with flow parameters correspondingly adjusted to ensure that there is only a single particle at a time in an illumination spot provided by the light source. In other variations, other elements can be additionally or alternatively be shared between the subsystems 151, 155.

In an example, as shown in FIG. 10A, the imaging subsystem 151 and the fluorescence subsystem 155 share an objective lens 154 that simultaneously receives and transmits light originating from the first light source 152 and the second light source 157 toward an image sensor 156 and a photodetector 160, respectively. In the example, the imaging subsystem 151 and the fluorescence subsystem 155 further share a dichroic mirror 162 configured to transmit specific wavelengths of light from the objective lens 154, and to reflect other wavelengths of light from the objective lens 154 (e.g., to another light sensing module). The dichroic mirror 162 can be configured to reflect light emitted by fluorescent labels, in response to excitation, toward the photodetector 160 to generate the fluorescence dataset, and to transmit light from the first light source 152 directly toward the image sensor 156 to generate the morphology dataset. Alternatively, the dichroic mirror 162 can be configured to transmit light emitted by fluorescent labels toward the photodetector 160 and to reflect light from the first light source toward the image sensor 156. The dichroic mirror 162 is preferably a short-pass dichroic mirror, but can alternatively be a long-pass dichroic mirror or any other suitable dichroic mirror.

Figure 10B:
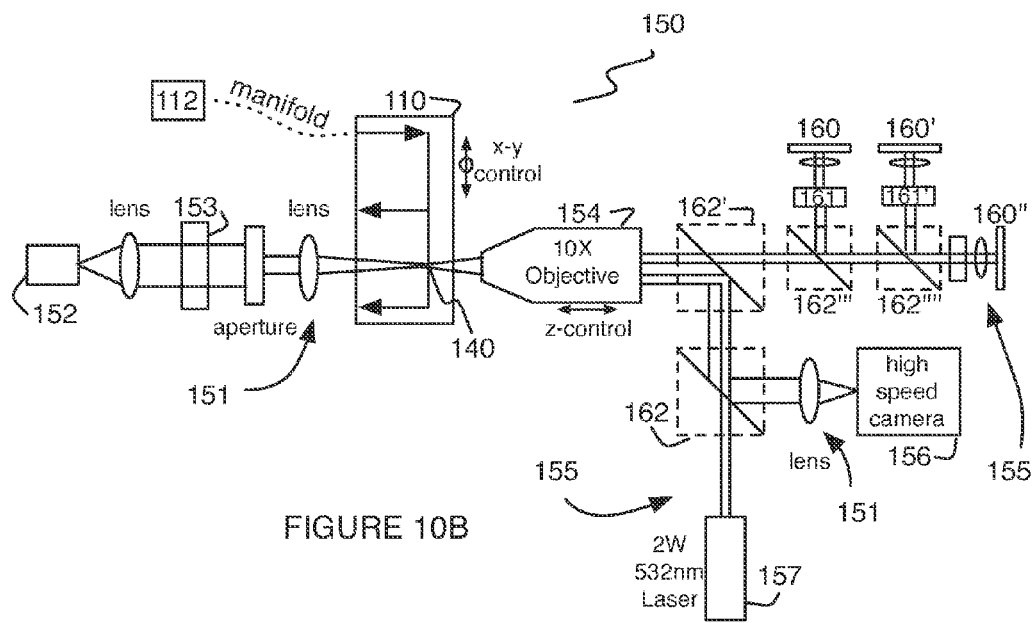

In another example, as shown in FIG. 10B, the imaging subsystem 151 and the fluorescence subsystem 155 share an objective lens 154 that simultaneously receives and transmits light originating from the first light source 152 and the second light source 157 toward an image sensor 156 and a photodetector 160, respectively. In this example, the detection module 150 includes a first xenon light source 152 configured to transmit light through a lowpass filter 153 and a plurality of lenses separated by an aperture and a lowpass filter 153, toward the deformation region 140 of the fluidic pathway 120, and through a 10× objective lens to be reflected off of a first and a second dichroic mirror 162, 162' toward an image sensor 156. In this example, the detection module 150 further includes a second 532 nm laser light source 157 configured to transmit light through the first dichroic mirror 162, to be reflected off of the second dichroic mirror 162' toward the 10× objective lens. Excitation light from the second light source 157 is configured to focus upon the deformation region 140, and light emitted from fluorescent labels at the deformation region is configured to be transmitted back through the second dichroic mirror 162', through a bandpass filter and a lens and a bandpass filter, toward a photodetector 160. In variations of this example, light emitted from fluorescent labels at the deformation region 140 can be transmitted through the second dichroic mirror 162' and toward additional photodetectors 160', 160" by additional dichroic mirrors 162''', 162'''', bandpass filters, and lenses, wherein the photodetectors 160, 160', and 160" are configured to receive different wavelengths (or ranges of wavelengths) of light.

Figure 10C:
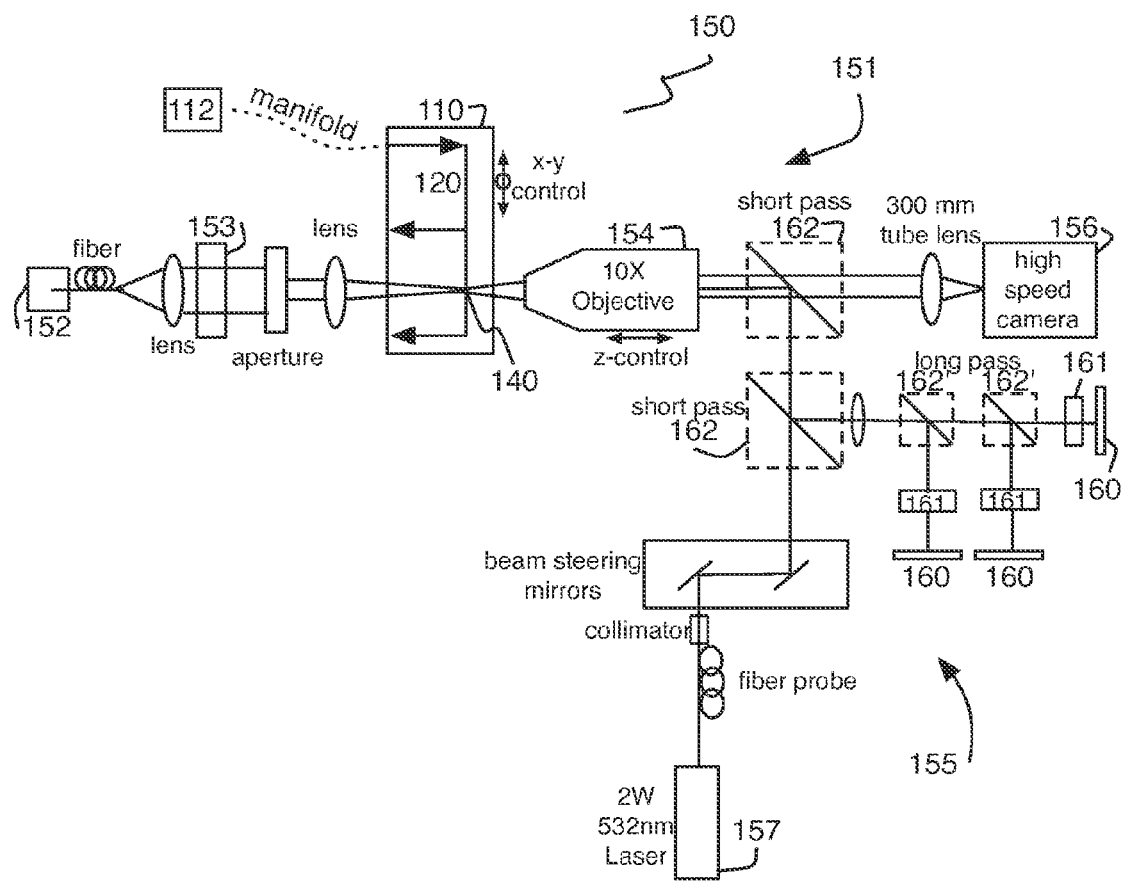

In still another example, as shown in FIG. 10C, the imaging subsystem 151 and the fluorescence subsystem 155 share an objective lens 154 that simultaneously receives and transmits light originating from the first light source 152 and the second light source 157 toward an image sensor 156 and a photodetector 160, respectively. In this example, the detection module 150 includes a first light source 152 configured to transmit light through a lowpass filter 153 and a plurality of lenses separated by an aperture and a lowpass filter 153, toward the deformation region 140 of the fluidic pathway 120, and through a 10× objective lens 154 and a first short pass dichroic mirror 162 toward an image sensor 156. In this example, the detection module 150 further includes a second 532 nm laser light source 157 coupled to a fiber probe and configured to transmit light through collimating optics, through a beam steering element (e.g., a set of mirrors, as in FIG. 10C, or an x-y translating fiber mount), through a second short pass dichroic mirror 162, to be reflected off of the first short pass dichroic mirror and through the objective lens 154 to the deformation region 140. Light emitted from fluorescent labels at the deformation region is then configured to pass into the objective lens 154, to be reflected off the first short pass dichroic mirror 162 and the second dichroic mirror 162 to a set of long pass dichroic mirrors 162'. The set of long pass dichroic mirrors is configured to reflect and transmit specific wavelengths of light, through band-pass filters 161, toward specific photodetectors 160 for fluorescence detection, as shown in FIG. 10C.

In other variations, the detection module 150 can include any other suitable element(s) and/or configuration of elements that allows simultaneous or near simultaneous generation of the morphology dataset and the fluorescence dataset. In examples, the detection module can comprise any one or more of a beam splitter, an aperture, an additional dichroic mirror, a collimator, any number of lenses, and any other suitable element configured to manipulate light from a light source. Furthermore, any element can be coupled to an actuator (e.g., manual, automatic actuator) that enables alignment of optics and/or adjustment of focal lengths. In one example, the objective lens 154 can be coupled to a linear actuator (e.g., a z-axis control) that enables adjustment along one or more axes. Additionally or alternatively, the substrate itself 110 can be coupled to an actuator (e.g., by a stage) that provides linear actuation along one or more axes (e.g., by an x-y control).

1.3.1 System—Detection Module Alternatives

In some embodiments, the detection module 150 can additionally or alternatively include a one-dimensional detection module 163 configured to facilitate an increase in data acquisition rates and a decrease in analysis times. The one-dimensional detection module 163 functions to enable extraction of particle deformation characteristics, without generation of two-dimensional or three-dimensional data, in order to generate a morphology dataset.

Figure 11A:
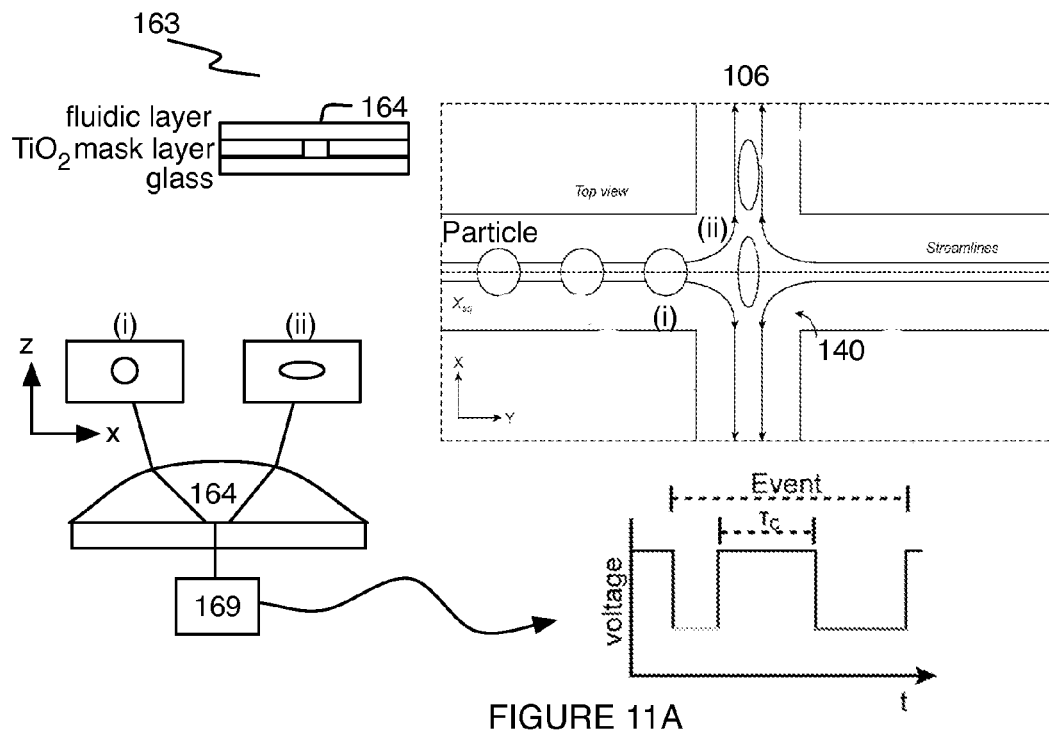
FIG. 11A-11C depict alternative variations of a detection module in an embodiment of a system for deforming and analyzing particles.

In a first variation, as shown in FIG. 11A, the one-dimensional detection module 163 comprises an optical mask including a set of slits 164 configured to facilitate generation of particle transit time measurements with an increased signal-to-noise ratio. In the first variation, the optical mask preferably includes at least one slit situated upstream of the deformation region 140 and at least one slit situated downstream of the deformation region, which enables detection of a difference in a particle dimension (e.g., cell length) before and after particle deformation. A photodetector 169 configured to receive light through the optical mask, and to generate an electrical signal (e.g., a voltage drop) upon a change in incident light produced by a particle passing a slit of the optical mask, can be used to provide a correlation between an electrical signal (e.g., voltage drop, duration of a voltage drop) and a particle dimension (e.g., cell length). In the first variation, the slit width is governed by an anticipated particle dimension, and in specific examples, is preferably smaller than the smallest expected cell size in order to directly infer a cell dimension from the one-dimensional detection module 163. However, the optical mask can alternatively include a slit with a width greater than an anticipated particle dimension (e.g., to facilitate optical mask fabrication), and signals generated by a photodetector cooperating with the optical mask can be configured to produce deformation measurements based upon deconvolution with mean transit signal characteristics. In an alternative to the first variation, the one-dimensional detection module 163 comprises an optical mask including a set of patterns and a photodetector 169 configured to receive light through the optical mask, and to generate an electrical signal (e.g., a voltage drop, duration of a voltage drop) upon a change in incident light produced by a particle passing a pattern of the optical mask. In this alternative, a signal produced by the photodetector can be matched to a library of generated signals in order to extract particle dimensional parameters (e.g., cell length). However, the optical mask can alternatively include any other features configured to enable detection of a particle dimension without generation of two-dimensional or three-dimensional data.

Figure 11B:
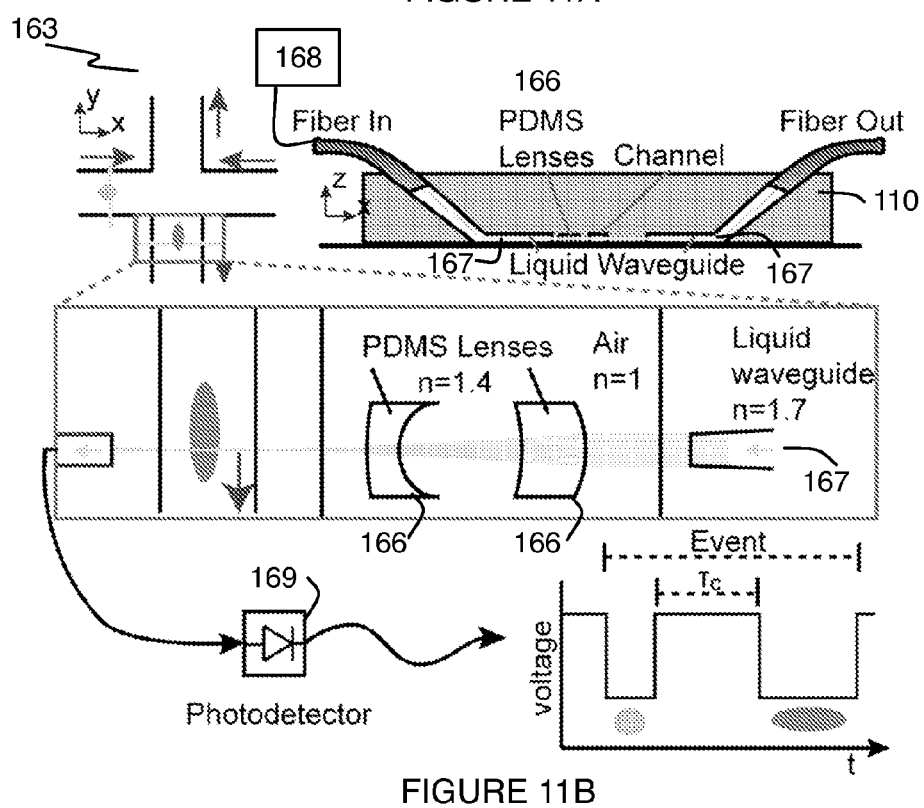

In a second variation, the one-dimensional detection module 163 can comprise a set of lenses 166 with a liquid waveguide 167 coupled to a light source 168 (e.g., fiber optic coupled to a light source) and a detector 169, wherein a light ribbon generated by light passing from the light source 168, through the liquid waveguide 167, and through the set of lenses 166, can be used to generate transit time measurements resulting from a voltage drop induced by a particle passing the light ribbon. The liquid waveguide 167 and the set of lenses 166 are preferably integrated (e.g., physically coextensive) with the substrate 110, as shown in FIG. 11B; however, the liquid waveguide 167 and/or the set of lenses 166 can alternatively be configured in any other suitable alternative manner. Furthermore, the light ribbon can be directed directly to the detector 169, such that the light source 168 is directly opposed to the detector 169 as in FIG. 11B, or can be directed between the light source 168 and the detector 169 in any other suitable manner (e.g., using positionally offset waveguides). In a specific example of the second variation, the liquid waveguide comprises high-refractive index oil (e.g., index=1.6), and the lenses have a refractive index of 1 to facilitate generation of the light ribbon.

Figure 11C:
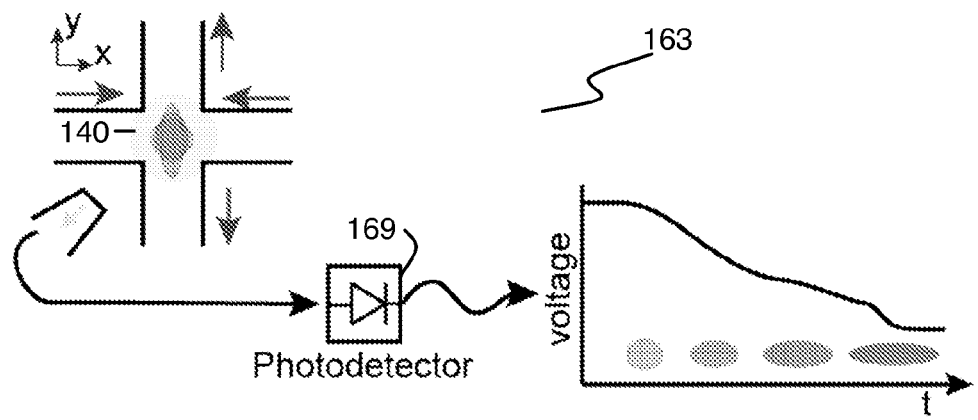

In a third variation, the one-dimensional detection module 163 can comprise a detector 169 configured to enable generation of a particle dimension measurement during deformation using forward and/or side-scatter measurements, as shown in FIG. 11C. Scattered-light features (e.g., profiles, parameters) detected as a particle enters and leaves the deformation region 140 can be used to infer particle deformation characteristics. For example, light scattering, as detected by the detector 169, can produce a voltage drop that increases in magnitude with increasing deformation, as shown in FIG. 11C. At least a portion of the third variation of the one-dimensional detection module 163 can be integrated into the substrate 160; however, the third variation of the one-dimensional detection module 163 can alternatively be physically distinct from the substrate 110.

Figure 12A:
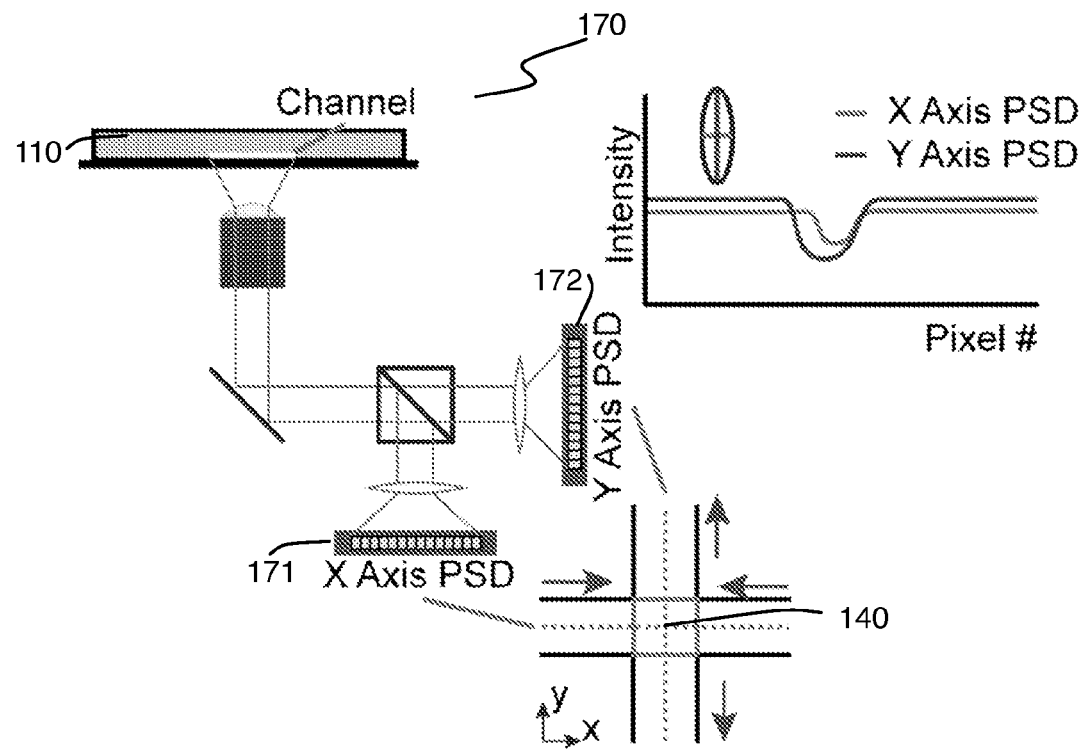
FIGS. 12A-12C depict alternative variations of a detection module in an embodiment of a system for deforming and analyzing particles.
Figure 12B:
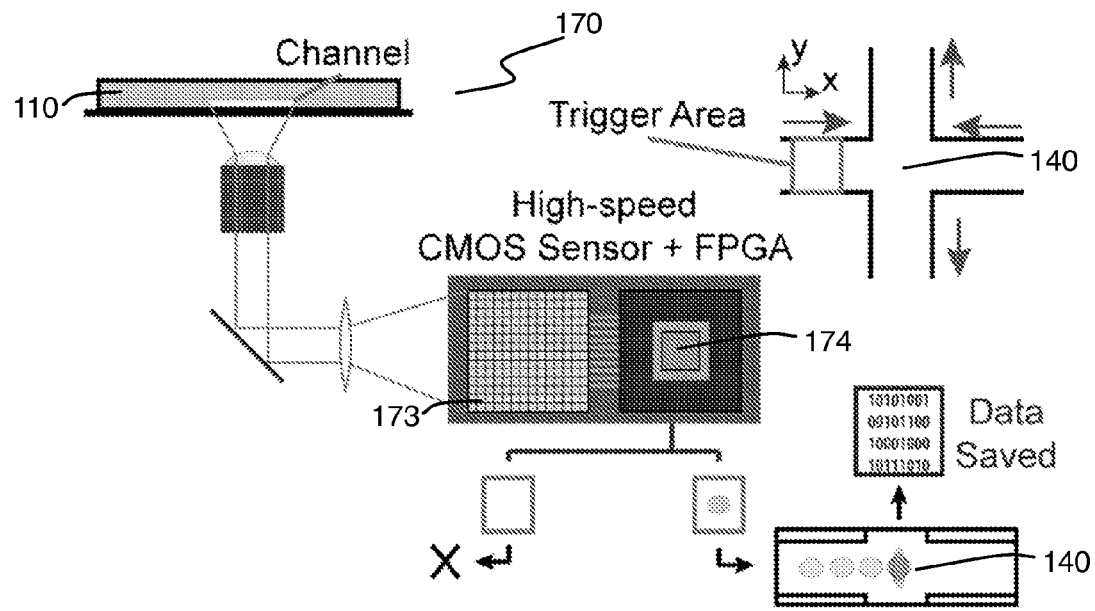

In still other embodiments, the detection module 150 can additionally or alternatively include a two-dimensional detection module 170 configured to facilitate an increase in data acquisition rates and a decrease in analysis times. The two-dimensional detection module 170 functions to enable rapid extraction of particle deformation characteristics based upon alternative element compositions and/or configurations, in order to generate a morphology dataset. An exemplary two-dimensional detection module 170 is illustrated in FIG. 12A.

In one embodiment, the two-dimensional detection module 170 includes a first position-sensitive detector 171 (PSD) configured to detect a particle deformation along a first axis (e.g., x-axis deformation of a particle) as the particle is deformed within the deformation region 140, and a second PSD 172, oriented orthogonally to the first PSD 171 and configured to detect a particle deformation along a second axis (e.g., y-axis deformation of a particle) as the particle is deformed within the deformation region 140. The first and the second PSDs 171, 172 are each preferably configured to generate an electrical signal (e.g., voltage drop, duration of a voltage drop) indicative of a particle dimension (e.g., length) during particle deformation within the deformation region 140, as shown in FIG. 12A. Signals provided by the first PSD can be passed in a first channel and signals provided by the second PSD can be passed in a second channel, and in an alternative variation, signals provided by the first PSD and the second PSD 171, 172 can be multiplexed in a single channel to reduce resource requirements during signal processing. In a specific example of the first variation, the first and the second PSDs are defined by a 100 kHz bandwidth and a 2 micrometer spatial resolution, configured to enable deformation measurements within a 70 micrometer×70 micrometer region of the deformation region 140.

Figure 12C:
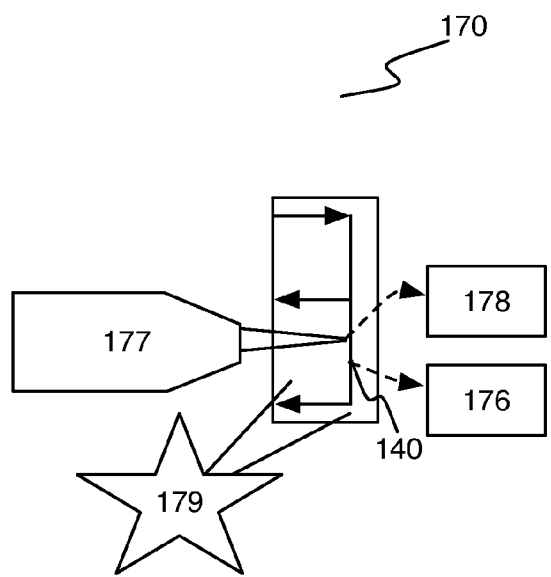

In a second embodiment, as shown in FIG. 12C, the two-dimensional detection module 170 comprises an image sensor 173 and a field programmable gate array (FPGA) 174 configured to cooperate with the image sensor 173 to identify a particle event, and to selectively trigger signal capture of a particle undergoing deformation upon identification of the particle event. The image sensor 173 is preferably configured to capture image data at the deformation region 140, but can be configured in any other suitable manner. In the second variation of the two-dimensional detection module 170, the detection module 150 can thus avoid collecting a substantial number of blank frames (i.e., frames not providing any particle-related data), which significantly reduces computational workload. In a specific application, the FPGA can be configured to screen a trigger region 175 upstream of the deformation region 140, and upon identification of a particle within the trigger region 175 (i.e., the particle event) by the FPGA, the image sensor 173 can be configured to capture image data of the particle undergoing deformation within a limited time window (e.g., 30 frames).

In a third embodiment, the two-dimensional detection module 170 comprises an image sensor 176 configured to capture deformation of a particle within the deformation region 140, a light source 177 configured to emit light toward particles entering the deformation region 140 at a location upstream of the deformation region, a photodetector 178 configured to receive light from the light source 177, thus facilitating identification of a particle about to enter the deformation region 140, and a strobe 179 configured to flash multiple times in synchronization with motion of the particle within the deformation region 140. Flashing of the strobe 179 thus enables capturing of multiple positions and/or deformations of a particle within a single image frame, which allows a single image frame to provide more useful data related to particle deformation characteristics. The strobe can be configured to flash multiple times, with a fixed time interval between strobe flashes, and can alternatively be configured to flash without a fixed time interval between strobe flashes, as guided by the photodetector 178. In a specific example of the third variation, the image sensor 176 is characterized by a frame rate of 2,000-10,000 frames per second and a field of view of 150 micrometer×150 micrometer. The light source 177 in the example is a laser focused upstream of the deformation region 140, and the photodetector 178 comprises at least one of a photomultiplier tube (PMT) and an amplified photodiode configured to detect scattered laser light produced when a particles passes through the laser beam. The scattered light, as detected by the photodetector 178 in the specific example, is used to trigger the strobe 179 to flash twice (e.g., with a 500 ns exposure time) with a fixed time interval corresponding to a time required for the particle (i.e., the particle scattering light from the laser) to transit between two positions about the deformation region 140. In the specific example, each image frame thus comprises information related to two positions and two morphological characterizations of a particle undergoing deformation in the deformation region 140.

Other alternative variations of the detection module 150 can include any other suitable element(s) or combination of elements that enable measurement and detection of particle morphological data that yield deformation based upon single-dimension acquisition and/or multi-dimension acquisition.

1.4 System—Other Elements

Referring back to FIG. 1, the processor 180 functions to transform the morphology dataset into a set of deformation characteristics characterizing deformation of each particle in the plurality of particles, to transform the fluorescence dataset into a set of fluorescence parameters characterizing biomolecular properties of each particle in the plurality of particles, and to generate an analysis based upon the set of deformation characteristics and the set of fluorescence parameters. Preferably, the morphology dataset and the fluorescence dataset are temporally synchronized, to facilitate matching of image and fluorescence data with specific particles in the plurality of particles; however, the image and the fluorescence datasets can be synchronized by any other metric. As such, the processor 180 preferably includes a first module 181 configured to extract a set of deformation characteristics from the morphology dataset, a second module 182 configured to extract a set of fluorescence parameters from the fluorescence dataset, a third module 183 configured to synchronize the morphology dataset and the fluorescence dataset, and a fourth module 184 configured to generate an analysis based upon the set of deformation characteristics and the set of fluorescence parameters. It should be understood that, in some alternative embodiments, any of the modules 181, 182, 183, 184 may be combined with one another. The modules 181, 182, 183, 184 can include instructions or algorithms executed by the processor 180. These modules 181, 182, 183, 184 may be stored in memory or other data storage device operatively coupled to the processor 180. Further, while reference is made to a single processor 180 it should be understood that one or more additional processors 180 may function together as a single processing unit.

Figure 13A:
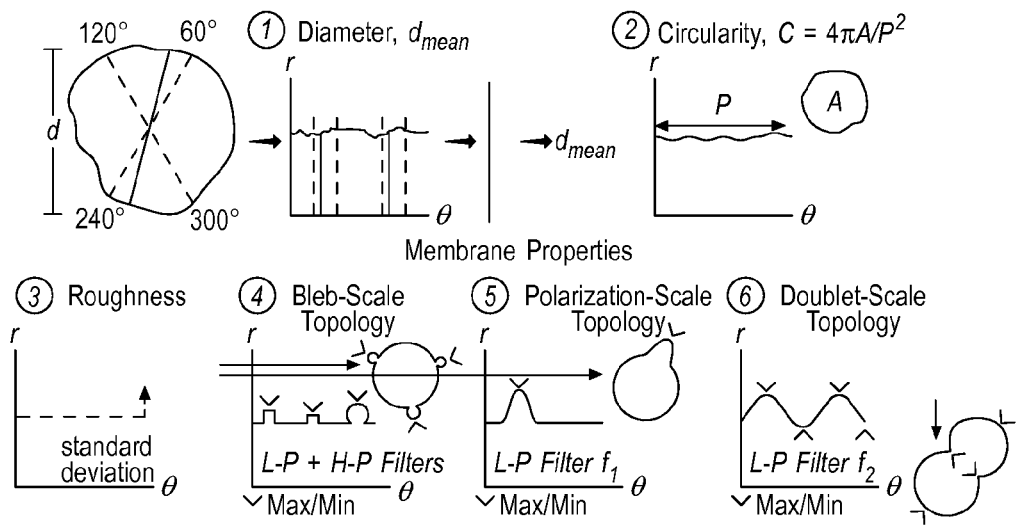
FIG. 13A-13C depict example particle characteristics extracted using an embodiment of a system for deforming and analyzing particles.
Figure 13B:
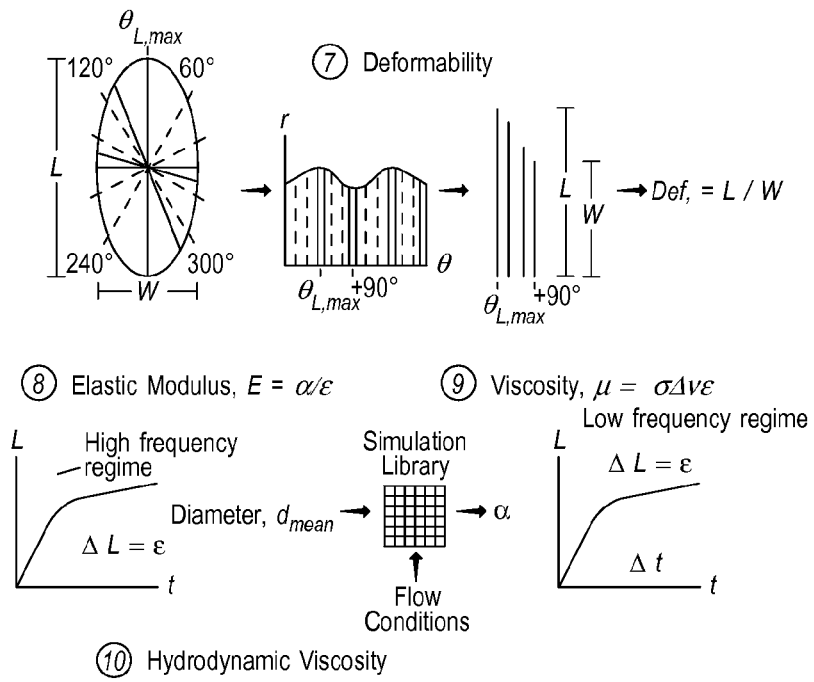
Figure 13B:
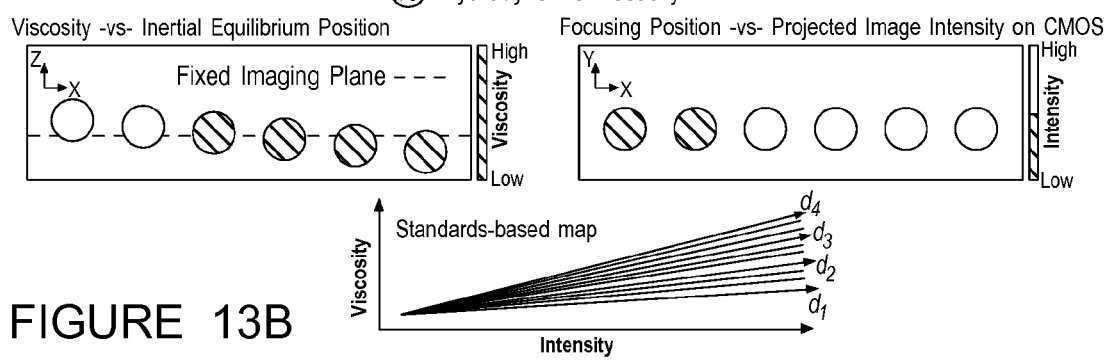
Figure 13C:
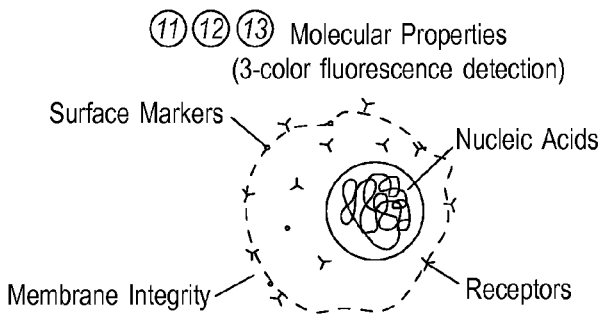

The first module 181 functions to extract a set of deformation characteristics from the morphology dataset that can be used to synchronize the morphology dataset with the fluorescence dataset, and can be used to generate an analysis by the fourth module 184. The first module 181 can extract the set of deformation characteristics continuously or near-continuously and in real time (e.g., such that deformation of a particle is tracked in real time); however, the first module 181 can alternatively be configured to extract characteristics non-continuously and/or in non-real time. The set of deformation characteristics preferably provide morphological and/or structural characteristics indicative of phenotype, such as nuclear size, chromatin decondensation, cytoskeletal disassembly/fluidization, and membrane compromise/lysis. The set of deformation characteristics can thus provide information related to the cell membrane and/or the cell nucleus. In some variations, the set of deformation characteristics can include any one or more of: particle deformability (e.g., a ratio of particle length to width), particle elastic modulus (e.g., a ratio of strain measured in an initial high frequency deformation regime, to stress provided by a library of simulated fluid-induced stresses and particle dimensions), particle viscosity (e.g., a measurement of strain rate in a low frequency deformation regime), particle hydrodynamic viscosity (e.g., based upon an inertial equilibrium position of a particle), particle circularity (e.g., based upon a ratio of particle projected area to particle projected perimeter), particle roughness (e.g., a standard deviation of particle radius measurements), particle size (e.g., volume, area, diameter, etc.), particle topological characteristics, particle asymmetry, and any other suitable morphological or structural characteristic, as shown in FIGS. 13A-13C. The first module 181 can also be configured to extract baseline morphological particle characteristics, including one or more of: initial particle volume, initial particle diameter, initial particle asymmetry, and any other suitable baseline characteristic. Extracting particle characteristics can be performed as in U.S. Pub. No. 2013/0177935, entitled "Method and Device for High Throughput Cell Deformability Measurements", or in any other suitable manner. In variations wherein the first module 181 is configured to extract baseline morphological particle characteristics, the baseline characteristics can be used to normalize the set of deformation characteristics for each particle in the plurality of particles, and/or can be used by the fourth module 184 to generate the analysis in any other suitable manner. In one embodiment, the first module 181 outputs a sequence indicator (e.g., frame number(s) of an image used to extract a deformation characteristic, time stamp, etc.) along with at least one extracted deformation characteristic for each particle in the plurality of particles; however, the first module can provide any other suitable output. In a specific example, the first module 181 is configured to output particle deformability along with the frame number(s) of an image used to extract deformability.

The second module 182 functions to extract a set of fluorescence parameters from the fluorescence dataset that can be used to synchronize the fluorescence dataset with the morphology dataset, and can be used to generate an analysis by the fourth module 184. The second module 182 can extract the set of fluorescence parameters continuously or near-continuously and in real time (e.g., such that fluorescence of a particle is tracked in real time); however, the first module 181 can alternatively be configured to extract characteristics non-continuously and/or in non-real time. The set of fluorescence parameters preferably provide characteristics indicative of biomolecular phenotype (e.g., surface markers, nucleic acid composition, membrane integrity, receptor characteristics) and can include any one or more of: an intensity of emitted light (e.g., average intensity, peak intensity), a wavelength of emitted light, kinetic parameters of fluorescence, and any other suitable fluorescence parameter. The second module 182 can also be configured to extract baseline fluorescence parameters (i.e., prior to particle deformation), including one or more of: initial intensity (e.g., initial average or peak intensity), initial emitted wavelength prior to deformation, initial kinetic parameter(s) prior to deformation, and any other suitable baseline parameter. In variations wherein the second module 182 is configured to extract baseline fluorescence parameters, the baseline parameters can be used to normalize the set of fluorescence parameters for each particle in the plurality of particles, and/or can be used by the fourth module 184 to generate the analysis in any other suitable manner. Preferably, the second module 182 outputs a sequence indicator (e.g., time stamp, frame number(s) of an image used to extract a fluorescence parameter, etc.) along with at least one extracted fluorescence parameter for each particle in the plurality of particles; however, the first module can provide any other suitable output. In a specific example, the second module is configured to output a continuous signal of intensity and time. For example, the signal may comprise a continuous voltage signal from a PMT as described herein. Peaks corresponding to the detected fluorescent particles may be extracted from the generated dataset using the second module 182.

Figure 14:
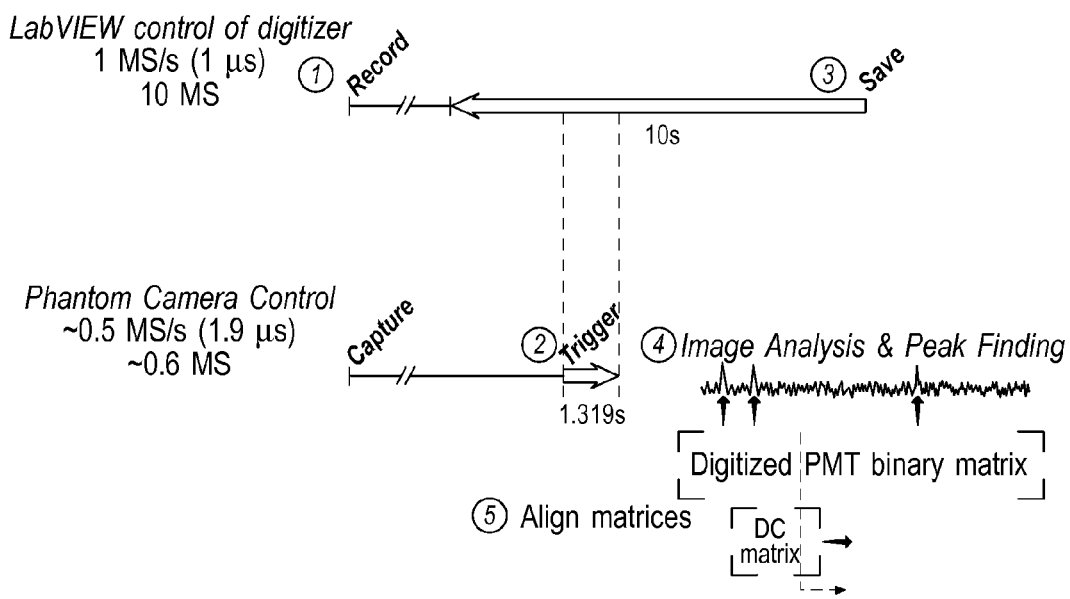
FIG. 14 depicts an example synchronization method for an embodiment of a system for deforming and analyzing particles.

The third module 183 functions to synchronize the morphology dataset and the fluorescence dataset. Preferably, the morphology dataset and the fluorescence dataset are output from the image sensor 155 and the photodetector 160 using the same clock, such that time points across the image data and the fluorescence data are substantially synchronized. Synchronization may be accomplished by subtracting an elapsed time that corresponds to the time delay when the particle passes from the fluorescence interrogation region to the morphology detection region. In some variations, however, the morphology dataset and the fluorescence dataset may not be associated with the same clock, motivating synchronization of the morphology dataset and the fluorescence dataset. The third module 183 can be configured to perform any suitable signal conditioning step (e.g., noise removal by filtering and peak-finding). In one specific example, wherein the first module 181 is configured to output particle deformability along with a frame number of an image used to extract deformability and the second module 182 is configured to output a continuous signal of intensity and time, the third module 183 is configured to apply signal filters to remove signal noise and apply a peak-finding algorithm to identify a time-dependent sequence of particles. A sequence matching or cross-correlation algorithm, an example of which is shown in FIG. 14, is then used to align the event vs. time signals of the morphology dataset with the event vs. time signals of the fluorescence dataset. In variations of the example, calibration particles (e.g., rigid or deformable fluorescent calibration microspheres) characterized by identifiable deformability and fluorescence signatures can be used to synchronize the morphology dataset with the fluorescence dataset, irrespective of time stamps. In still other variations, relationships between deformability (or any other suitable deformation characteristic) and emitted fluorescence intensity can be used to synchronize the sets of data. However, the morphology dataset and the fluorescence dataset can be synchronized in any other suitable manner.

The fourth module 184 functions to generate an analysis based upon the set of deformation characteristics and the set of fluorescence parameters. The analysis can comprise a correlation between mechanical and biochemical/biomolecular markers for the particles of interest, which can be used to identify mechanical (e.g., deformation) characteristics, fluorescence parameters, and/or combinations of mechanical and fluorescence parameters useful for characterizing particles of the plurality of particles. In specific applications, the analysis generated by the fourth module 184 can be used to identify activation states of specific cell types (e.g., blood mononuclear cell activation by mitogens or inflammatory processes, granulocyte activation with cytokines or blood stream infections, as identified by deformability and surface expression of activation markers), with important implications in label-free monitoring of diseases, diagnosis of diseases, treatment of diseases, and prediction of transplant rejection. In additional applications, the analysis generated by the fourth module 184 can be used to identify phenotypic connections between stem cells and cancers (e.g., Jurkat and HL60), used to identify differentiation indicators for stem cells, and used for identification of subpopulations of cells within diverse populations of cells in body fluid samples from healthy or diseased patients (e.g., resting or activated leuokocytes, PBMCs, and granulocytes as in blood, or pleural fluid). As such, the fourth module 184 can be used to aggregate a library of data of multiple types of phenotypic markers (e.g., mechanical, deformation, fluorescence, etc.) for a variety of biological particles, using a high-throughput approach.

The fourth module 184 can be configured to conduct a statistical analysis (e.g., correlation, t-test, ANOVA, etc.), which functions to investigate relationships between deformation and fluorescence parameters. Additionally or alternatively, classification and regression trees (CARTs) generated by the fourth module 184 can be used, with deformation and fluorescence parameters used to enhance identification. Receiver operating characteristic (ROC) curves can be used to assess an ability to correctly identify particles for purposes of generating predictive models. Furthermore, linear discriminate analyses (or other machine learning approaches) can be used to identify similarities and/or differences between different sample volumes, which can be used, for example, to stratify samples from different patients. In some variations, the processor 180 can further be configured to render the analysis at a user interface (e.g., as a flow cytometry 2D or 3D density plot of single cells, etc.) such as a display or monitor.

As shown in FIG. 1, the system 100 can further comprise a filter 190 located upstream of the delivery region 130. The filter 190 functions to separate particles of interest from other particles or debris in the sample volume and to allow the particles of interest to pass into the fluidic pathway 120. Preferably, the filter 190 is configured between an inlet 104 and the fluidic pathway 102, such that the sample volume is substantially filtered prior to delivery into the fluidic pathway 120, delivery region 130, and/or deformation region 140. Additionally or alternatively, the system 100 can include a filter 190 positioned at any other suitable location of the system 100, and/or any suitable number of filters in any other suitable configuration. The filter 190 preferably separates the particles based upon size (e.g., using suitably sized pores in a porous structure or mesh); however, the filter 190 can alternatively separate particles of interest from other particles in the sample volume based upon any other suitable separation mechanism (e.g., chemical, affinity moiety, electric, magnetic, etc.).

Also shown in FIG. 1, the system 100 can further comprise a processed sample volume receiver 195, which functions to receive a processed sample fluid from an outlet 106 of the substrate 110. As briefly described earlier, the processed sample volume receiver 195 can be a waste chamber configured to fluidly couple to the outlet 106 to collect the processed sample fluid as waste. Furthermore, the waste chamber can be integrated (e.g., physically coextensive, of unitary construction) with the substrate 110 in any suitable manner. Alternatively, the processed sample volume receiver 195 can be configured to collect and transmit the processed sample volume, including the plurality of particles, to another module for additional assays and analyses. As such, the processed sample volume receiver can comprise one or more conduits and/or valves that facilitate sample transmission. In still other variations, the processed sample volume receiver 195 can be a composite receiver that receives a portion of the sample volume as waste, and facilitates collection of another portion of the sample volume for further analyses.

In some variations, the system 100 can further comprise a storage module 197 with accessible memory, which functions to receive and/or store at least one of the morphology dataset, the fluorescence dataset, an analysis, system 100 parameters (e.g., flow parameters, detection module parameters, etc.), sample volume identifiers (e.g., name, contents, date), and module algorithms. The accessible memory permits a user to access stored information about sample runs using the system 100 and the system parameters that were utilized during those runs. Any stored information is preferably accessible by a user and/or any other suitable entity. The storage module can be implemented using any suitable computing device (e.g., desktop computer, hardware storage device, server, cloud).

The system 100 can, however, include any other suitable element(s) or combination of elements that facilitate the deformation, assaying, and/or analysis of particles of a sample volume. As a person skilled in the art will recognize from the previous detailed description and from the figures and claims, modifications and changes can be made to the embodiments of the system 100 without departing from the scope of the system 100.

2. Method

Figure 15:
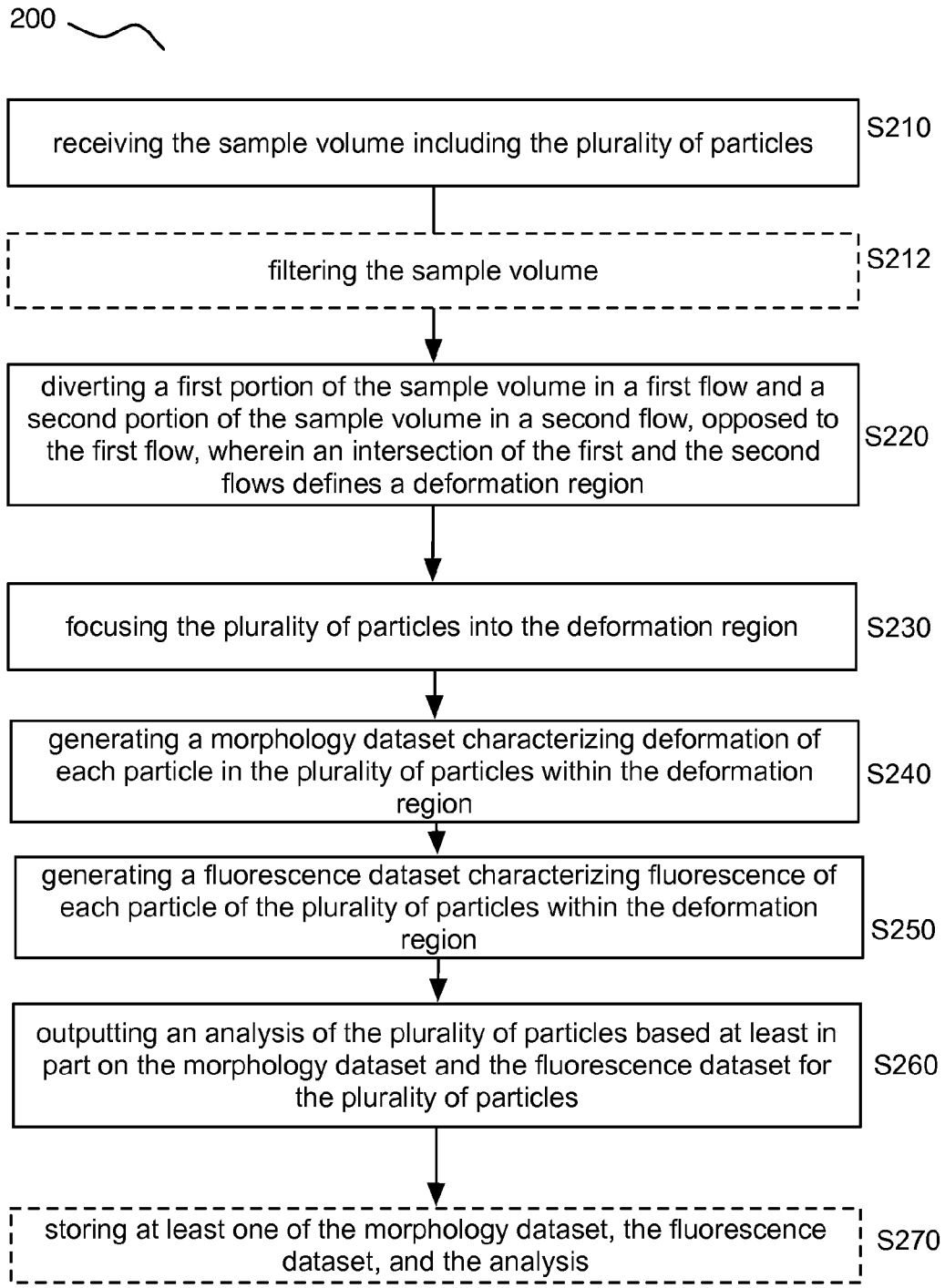
FIG. 15 is a flowchart of an embodiment of a method for deforming and analyzing particles.

As shown in FIG. 15, a method 200 for deforming and analyzing a plurality of particles carried in a sample volume includes: receiving the sample volume including the plurality of particles S210; diverting a first portion of the sample volume in a first flow and a second portion of the sample volume in a second flow, opposed to the first flow, wherein an intersection of the first and the second flows defines a deformation region S220; focusing the plurality of particles into the deformation region S230; generating a morphology dataset characterizing deformation of each particle in the plurality of particles within the deformation region S240; generating a fluorescence dataset characterizing fluorescence of each particle of the plurality of particles within the deformation region S250; and outputting an analysis of the plurality of particles based at least in part on the morphology dataset and the fluorescent dataset for the plurality of particles S260.

The method 200 functions to enable the deformation of single particles in a high-throughput and consistent manner, with the ability to simultaneously generate and analyze multiple data types characterizing the single particles. Preferably, the method 200 further functions to enable the generation of data that directly correlates surface biomarkers of phenotype with mechanical properties at the single-particle level. This can allow the generation of a direct quantitative comparison between biomolecular properties and mechanical properties. Preferably, the method 200 is used to process and analyze biological particles, such as cells, and in specific applications, the method 200 can be used to analyze leukocyte activation, stem cell differentiation, and cancer cell malignancy by way of correlating cellular deformation with biomolecular phenotypes using fluorescence assays. However, the system 100 can alternatively be used to process, deform, and analyze any other suitable biological particle or non-biological particle using any other suitable analysis.

Block S210 recites: receiving the sample volume including the plurality of particles, and functions to receive a sample volume, including the plurality of particles, to initiate processing and analysis of the plurality of particles. The sample volume is preferably received at an inlet of a substrate, using a pump, as in an embodiment of the system 100 described above; however, the sample volume can be received and/or delivered in any other suitable manner. In some variations, Block S210 can further include filtering the sample volume S212, as shown in FIG. 15, which functions to separate particles of interest from other particles in the sample volume and to allow the particles of interest to pass into a fluidic pathway for further processing and analysis. Block S212 can be implemented using any suitable variation of the filter described above, or using any other suitable method of separating particles of interest from other particles in a sample volume.

Block S220 recites: diverting a first portion of the sample volume in a first flow and a second portion of the sample volume in a second flow, opposed to the first flow, wherein an intersection of the first and the second flows defines a deformation region. Block S220 functions to generate opposing flows configured to deform each particle in the plurality of particles. Block S220 is preferably implemented at an embodiment of the fluidic pathway of the system 100 described above, wherein the fluidic pathway includes at least two branches configured to generate the first and the second flows from the sample volume. Additionally or alternatively, an injected flow, not derived sample volume, can be used to generate at least one flow in the opposing flows. However, Block S220 can be implemented using any other suitable method of generating opposing flows, at least partially from a sample volume. In some variations, Block S220 can include diverting a first portion of the sample volume in the first flow, wherein the first flow comprises substantially all of the particles of interest and diverting a second portion of the sample volume in the second flow, wherein the second flow is substantially free of particles of interest; however, in other variations, the first flow and the second flow can both comprise a subset of the plurality of particles.

Block S230 recites: focusing the plurality of particles into the deformation region, and functions to transmit the plurality of particles, along at least one streamline into the deformation region, such that each particle in the plurality of particles experiences uniform flow conditions prior to deformation within the deformation region. Block S230 is preferably implemented at a delivery region in an embodiment of the system 100 described above, but can be implemented at any other suitable portion of a fluid pathway configured to focus particles. Preferably, any flow including particles of the plurality of particles is focused into the deformation region in Block S230; however, in alternative variations, Block S230 can omit focusing of any subset of the plurality of particles, and/or focusing of flows not including particles of the plurality of particles. In one embodiment, focusing in Block S230 includes focusing using inertial focusing in at least one of a confined curved channel and a channel including a set of height restrictions, as described above; however, focusing in Block S230 can comprise any one or more of: hydrodynamic focusing, focusing using a sheath fluid, dielectrophoretic focusing, ultrasonic focusing, magnetic focusing, and any other suitable focusing method.

Block S240 recites: generating a morphology dataset characterizing deformation of each particle in the plurality of particles within the deformation region, and functions to generate a dataset that can be used to extract a set of deformation characteristics for generation of an analysis based upon deformation characteristics. The morphology dataset is preferably generated in Block S240 using an embodiment of the detection module and imaging subsystem described above; however, the morphology dataset can additionally or alternatively be generated using any suitable module including an image sensor configured to capture image data for particles undergoing deformation. Preferably, the morphology dataset generated is characterized by a high frame rate, such that the morphology dataset characterizes multiple stages of deformation for each particle in the plurality of particles. Furthermore, the morphology dataset is preferably generated in a continuous manner and in real time; however, the morphology dataset can alternatively be generated in any other suitable manner.

Block S250 recites: generating a fluorescence dataset characterizing fluorescence of each particle of the plurality of particles within the deformation region, and functions to generate a dataset that can be used to extract a set of fluorescence parameters for generation of an analysis based upon fluorescence parameters. The fluorescence dataset is preferably generated in Block S250 using an embodiment of the detection module and fluorescence subsystem described above; however, the fluorescence dataset can additionally or alternatively be generated using any suitable module including a photodetector configured to detect light emitted by fluorescent labels being excited by excitation wavelengths of light. Preferably, the fluorescence dataset is generated in a continuous manner and in real time; however, the fluorescence dataset can alternatively be generated in any other suitable manner. Furthermore, Block S250 is performed concurrently with Block S240, such that the morphology dataset and the fluorescence dataset are simultaneously or nearly simultaneously generated, and deformation characteristics and fluorescence parameters can be temporally matched or otherwise synchronized to each particle in the plurality of particles.

Figure 16:
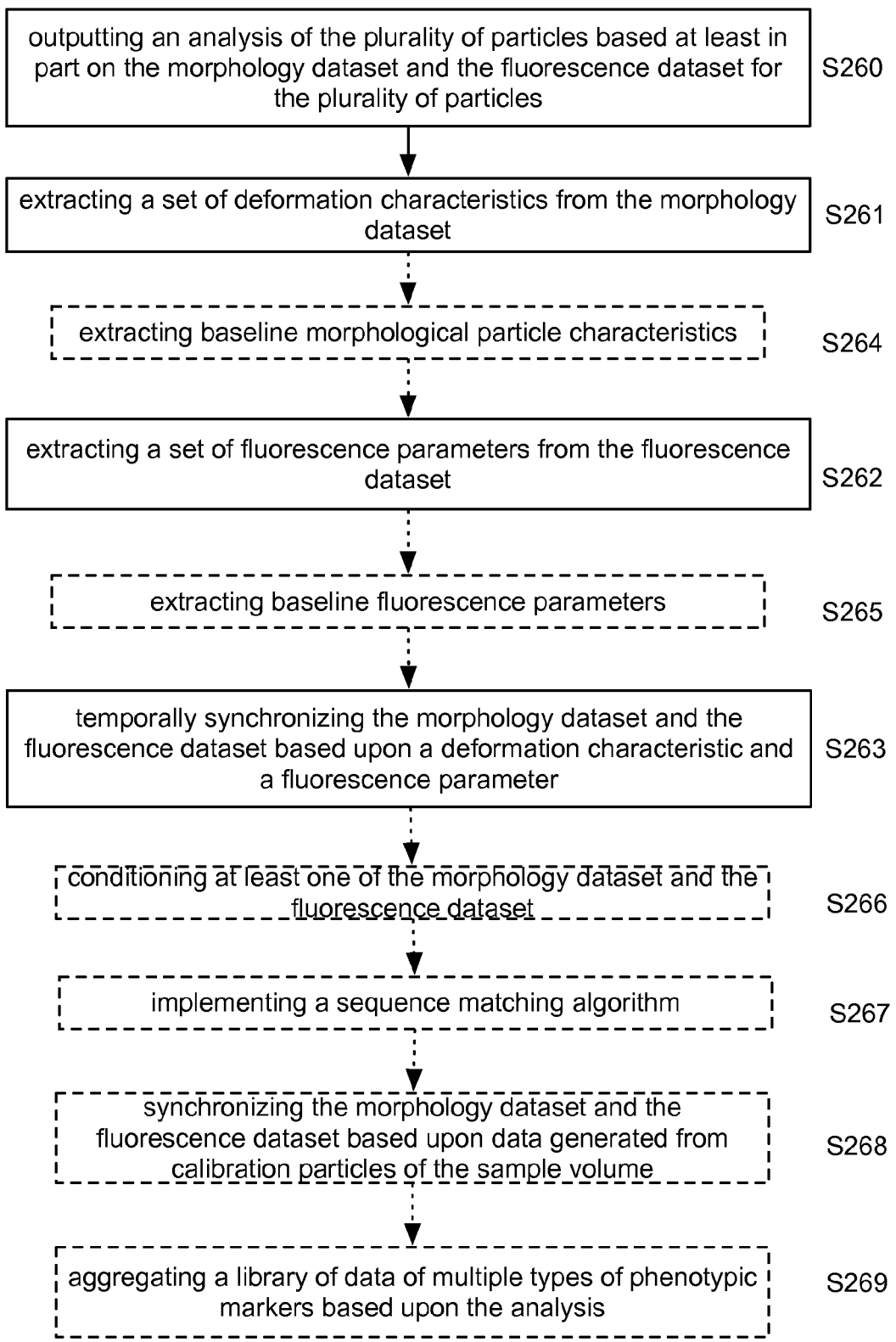
FIG. 16 is a flowchart of an embodiment of a method for deforming and analyzing particles.

Block S260 recites: outputting an analysis of the plurality of particles based at least in part on the morphology dataset and the fluorescent dataset for the plurality of particles S260, and functions to produce an analysis characterizing the particles of interest based upon multiple types of parameters (e.g., mechanical, deformation, fluorescence, biochemical, etc.). Block S260 is preferably implemented at an embodiment of the processor described above; however, Block S260 can additionally or alternatively be performed using any suitable processing element configured to generate an analysis based upon the morphology dataset and the fluorescence dataset. In variations, Block S260 can thus be implemented at a processor including a first module that extracts the set of deformation characteristics from the morphology dataset; a second module that extracts the set of fluorescence parameters from the fluorescence dataset; a fourth module configured to synchronize the morphology dataset and the fluorescence dataset based upon a deformation characteristic and a fluorescence parameter; and a fourth module configured to generate the analysis. As such, Block S260 can further include, as illustrated in FIG. 16: extracting a set of deformation characteristics from the morphology dataset S261; extracting a set of fluorescence parameters from the fluorescence dataset S262; and temporally synchronizing the morphology dataset and the fluorescence dataset based upon a deformation characteristic and a fluorescence parameter S263, as shown in FIG. 16.

In Blocks S260 and S261, the set of deformation characteristics preferably provide morphological characteristics indicative of phenotype, such as nuclear size, chromatin decondensation, cytoskeletal disassembly/fluidization, and membrane compromise/lysis. The set of deformation characteristics can thus include any one or more of: particle deformability, particle circularity, particle size (e.g., volume, area, etc.), particle asymmetry, and any other suitable morphological characteristic. In relation to Blocks S260 and S261 in FIG. 16, the method can additionally comprise extracting baseline morphological particle characteristics S264, including one or more of: initial particle volume, initial particle diameter, initial particle asymmetry, and any other suitable baseline characteristic. Extracting particle characteristics in Block S264 can be performed as in U.S. Pub. No. 2013/0177935, entitled "Method and Device for High Throughput Cell Deformability Measurements", or in any other suitable manner. In variations of the method 200 including Blocks S260, S261, and S264, the baseline characteristics can be used to normalize the set of deformation characteristics for each particle in the plurality of particles, and/or can be used to generate the analysis in any other suitable manner.

In Blocks S260 and S262, the set of fluorescence parameters preferably provide characteristics indicative of biomolecular phenotype and can include any one or more of: an intensity of emitted light (e.g., average intensity, peak intensity), a wavelength of emitted light, kinetic parameters of fluorescence, and any other suitable fluorescence parameter. Similar to variations of the method 200 including Block S264, the method 200 can also include extracting baseline fluorescence parameters S265 (i.e., prior to particle deformation), including one or more of: initial intensity (e.g., initial average or peak intensity), initial emitted wavelength prior to deformation, initial kinetic parameter(s) prior to deformation, and any other suitable baseline parameter. The baseline parameters can be used to normalize the set of fluorescence parameters for each particle in the plurality of particles, and/or can be used to generate the analysis in any other suitable manner.

In Blocks S260 and S263, synchronizing the morphology dataset and the fluorescence dataset can include conditioning at least one of the morphology dataset and the fluorescence dataset S266, wherein conditioning comprises at least one of noise removal by filtering and peak-finding. Block S266 can include applying signal filters to remove signal noise and applying a peak-finding algorithm to identify a time-dependent sequence of particles. Block S263 can further include implementing a sequence matching algorithm S267, an example of which is shown in FIG. 14, to align event vs. time signals of the morphology dataset with event vs. time signals of the fluorescence dataset. In variations, Block S263 can further include synchronizing the morphology dataset and the fluorescence dataset based upon data generated from calibration particles of the sample volume S268. In examples, the calibration particles can comprise rigid fluorescent calibration microspheres characterized by identifiable deformability and fluorescence signatures can be used to synchronize the morphology dataset with the fluorescence dataset, irrespective of time stamps. In still other variations, relationships between deformability (or any other suitable deformation characteristic) and emitted fluorescence intensity can be used to synchronize the sets of data in Block S263. However, the morphology dataset and the fluorescence dataset can be synchronized in any other suitable manner.

The analysis generated in Block S260 can comprise a correlation between mechanical and biochemical/biomolecular markers for the particles of interest, which can be used to identify mechanical (e.g., deformation) characteristics, fluorescence parameters, and/or combinations of mechanical and fluorescence parameters useful for characterizing particles of the plurality of particles. In specific applications, the analysis generated in Block S260 can be used identify activation states of specific cell lines (e.g., blood mononuclear cell activation by mitogens or inflammatory processes, granulocyte activation with cytokines or blood streams infections, as identified by deformability and surface expression of activation markers), with important implications in label-free monitoring of diseases, diagnosis of diseases, treatment of diseases, and prediction of transplant rejection. In additional applications, the analysis generated can be used to identify phenotypic connections between stem cells and cancers (e.g., Jurkat and HL60), used to identify differentiation indicators for stem cells, and used for identification of cells within a diverse populations of cells within diverse populations of cells in body fluid samples from healthy or diseased patients (e.g., resting or activated leuokocytes, PBMCs, and granulocytes as in blood, or pleural fluid). As such, Block S260 can be further include aggregating a library of data of multiple types of phenotypic markers based upon the analysis S269, wherein the library characterizes phenotypic markers (e.g., mechanical, deformation, fluorescence, etc.) for a variety of biological particles, using a high-throughput approach.

Generating an analysis in Block S260 can thus comprise conducting a statistical analysis (e.g., correlation, t-test, ANOVA, etc.) to investigate relationships between deformation and fluorescence parameters. Additionally or alternatively, Block S260 can include generating a classification and regression tree (CART) to enhance identification, and can further include using a receiver operating characteristic (ROC) curves to assess correct identification of particles Furthermore, linear discriminate analyses can be used in Block S260 to identify similarities and/or differences between different sample volumes, which can be used, for example, to stratify samples from different patients.

As shown in FIG. 15, the method can further comprise Block S270, which recites: storing at least one of the morphology dataset, the fluorescence dataset, and the analysis. Block S270 functions to receive data related to deformation characteristics of the plurality of particles, fluorescence parameters of the plurality of particles, and correlations between deformation and fluorescence parameters for each particle in the plurality of particles. Block S270 can additionally function to store system parameters used to generate the datasets and/or the analyses, and can further function to enable data transmission to a user or another entity involved with the analysis. Block S270 is preferably implemented using an embodiment of the storage module described above; however, Block S270 can be implementing using any other suitable storage module.

As a person skilled in the art will recognize from the previous detailed description and from the figures and claims, modifications and changes can be made to the preferred embodiments of the invention without departing from the scope of this invention defined in the following claims.

The invention claimed is:

1. A system for affecting a plurality of particles carried in a sample volume, the system comprising:
   a substrate defining an inlet, configured to receive the sample volume, and an outlet; and
   a fluidic pathway fluidly coupled to the inlet and the outlet and comprising:
      an upstream focusing region fluidically coupled to the inlet and configured to preferentially align the plurality of particles in one or more fluid streamlines contained within the upstream focusing region;
      a junction coupled to an output of the upstream focusing region, the junction comprising a central main branch channel oriented substantially collinear with the output of the upstream focusing region and a pair of side fluid siphoning channels located on opposing sides of the central main channel, wherein substantially all of the plurality of particles in the one or more fluid streamlines are shunted to the central main branch channel and the pair of side fluid siphoning channels are substantially devoid of particles; and
      a first merging region formed downstream of the junction by an intersection of the central main branch channel and the pair of side fluid siphoning channels.

2. The system of claim 1, wherein flow of fluid from the pair of side fluid siphoning channels into the central main branch channel at the intersection induces a shape change of one or more particles passing through the intersection.

3. The system of claim 1, wherein flow of fluid from the pair of side fluid siphoning channels into the central main branch channel at the intersection induces pinching of one or more particles passing through the intersection.

4. The system of claim 1, wherein flow of fluid from the pair of side fluid siphoning channels into the central main branch channel at the intersection changes the streamline position of one or more particles passing through the intersection.

5. The system of claim 1, wherein flow of fluid from the pair of side fluid siphoning channels into the central main branch channel at the intersection focuses the one or more particles passing through the intersection to a narrower distribution of fluid streamlines.

6. The system of claim 1, wherein the central main branch channel comprises a branch focusing region that focuses the one or more particles passing through to a smaller number of fluid streamlines.

7. The system of claim 6, wherein the branch focusing region comprises an inertial focusing region.

8. The system of claim 1, wherein the upstream focusing region comprises an inertial focusing region.

9. The system of claim 1, wherein the particles are not subject to substantial deceleration upon entering the first merging region.

10. The system of claim 1, further comprising a second merging region located downstream of the first merging region, the second merging region formed downstream of the junction by an intersection of the central main branch channel and the one or more additional siphoning channels.

11. The system of claim 1, wherein the central main branch channel has a fluid resistance that is greater than the fluid resistance of the pair of side siphoning channels.

12. The system of claim 1, wherein the plurality of particles comprise cells.

13. The system of claim 1, wherein the pair of side fluid siphoning channels intersect the central main branch channel in a substantially orthogonal configuration.

14. The system of claim 1, wherein the pair of side fluid siphoning channels intersect the central main branch channel in an off-axis configuration.

15. The system of claim 1, wherein the respective flow rates in the pair of side fluid siphoning channels are equal.

16. The system of claim 1, wherein the respective flow rates in the pair of side fluid siphoning channels are non-equal.

* * * * *